United States Patent
Bretscher et al.

(10) Patent No.: US 6,465,541 B2
(45) Date of Patent: Oct. 15, 2002

(54) RADIOPAQUE CATIONICALLY POLYMERIZABLE COMPOSITIONS COMPRISING A RADIOPACIFYING FILLER, AND METHOD FOR POLYMERIZING SAME

(75) Inventors: Kathyrn R. Bretscher, Minneapolis; Richard P. Rusin, Woodbury; Sumita B. Mitra, West St. Paul; Janis R. Gust; Cheryl A. Hayne, both of Minneapolis, all of MN (US); Dwight W. Jacobs, Hudson, WI (US); David A. Kaisaki, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/898,219

(22) Filed: Jul. 3, 2001

(65) Prior Publication Data

US 2002/0002214 A1 Jan. 3, 2002

Related U.S. Application Data

(62) Division of application No. 09/168,051, filed on Oct. 7, 1998, now Pat. No. 6,306,926.

(51) Int. Cl.$^7$ .......................... A61K 6/087; C08L 63/00; C08K 3/22; C08F 2/46
(52) U.S. Cl. ...................... 523/117; 106/35; 433/228.1; 522/15; 522/25; 522/81; 522/83; 522/908; 523/116; 523/459; 523/460; 524/492; 524/493
(58) Field of Search ........................ 433/228.1; 106/35; 522/15, 25, 81, 83, 908; 523/116, 117, 459, 460; 524/430, 492, 493

(56) References Cited

U.S. PATENT DOCUMENTS

| | | |
|---|---|---|
| 3,018,262 A | 1/1962 | Schroeder .................... 523/402 |
| 3,117,099 A | 1/1964 | Proops et al. ................ 528/361 |
| 3,729,313 A | 4/1973 | Smith .......................... 522/175 |
| 3,741,769 A | 6/1973 | Smith ............................ 522/25 |
| 3,808,170 A | 4/1974 | Rogers ........................ 523/117 |
| 4,090,936 A | 5/1978 | Barton .................. 204/159.18 |
| 4,175,972 A | 11/1979 | Crivello ................. 204/159.18 |
| 4,221,698 A | 9/1980 | Lee, Jr. et al. ........... 260/42.52 |
| 4,228,062 A | 10/1980 | Lee, Jr. et al. ........... 260/42.28 |
| 4,250,053 A | 2/1981 | Smith .......................... 262/426 |
| 4,256,828 A | 3/1981 | Smith .......................... 430/280 |
| 4,285,729 A | 8/1981 | Matsumaru ................... 501/78 |
| 4,314,827 A | 2/1982 | Leitheiser et al. ............. 51/298 |
| 4,318,766 A | 3/1982 | Smith .......................... 156/330 |
| 4,378,277 A | 3/1983 | Smith .................... 204/159.18 |
| 4,394,403 A | 7/1983 | Smith .......................... 427/73 |
| 4,503,169 A | 3/1985 | Randklev .................... 523/117 |
| 4,554,259 A | 11/1985 | Franklin et al. .............. 501/67 |
| RE32,073 E | 1/1986 | Randklev .................... 623/117 |
| 4,593,051 A | 6/1986 | Koleske ........................ 522/31 |

(List continued on next page.)

FOREIGN PATENT DOCUMENTS

| | | |
|---|---|---|
| AU | A-34512/95 | 5/1996 |
| DE | 2403211 | 7/1975 |
| DE | 2950221 A1 | 6/1980 |
| EP | 0 330 117 | 8/1989 |
| EP | 0 361 542 B1 | 4/1990 |
| EP | 0 429 250 A2 | 5/1991 |
| EP | 0 678 533 A2 | 10/1995 |
| EP | 0 728 790 A1 | 8/1996 |
| JP | 1-174523 | 7/1989 |
| JP | 5-33250 | 5/1993 |
| RU | 688193 | 9/1979 |
| RU | 78220 | 9/1981 |
| RU | 2057522 | 4/1996 |
| WO | WO 94/21190 | 9/1994 |
| WO | WO 95/14716 | 6/1995 |
| WO | WO 96/13538 | 5/1996 |
| WO | WO97/07900 | 3/1997 |

OTHER PUBLICATIONS

"CRC Handbook of Organic Photochemistry", vol. II, ed. J.C. Scaiano, pp. 335–339 (1989).

"Handbook of Epoxy Resins" by Lee and Neville, Mcraw–Hill Book Co., New York (1967), Chapters 2 and 3, pp. 2–1 to 2–32 and 3–1 to 3–24.

"Quantitative Chemical Analysis" Harris, 3rd Ed., 1991, W.H. Freeman, NY, pp. 490–493.

S.J. Gregg and K.S.W. Sing in "Adsorption, Surface Area, and Porosity", Academic Press Inc., 2nd Ed., London (1982) pp. 41–105.

"Practical Refractometry by Means of a Microscope" Roy M. Allen, $2^{nd}$ Edition, Cargille, NJ pp. 6–7.

Tang et al., "Study of Diisocyanate Modified EAM Resin for Orthodontics Adhesive," *Stomatol. Coll.*, $4^{th}$ *Mil. Med. Univ.*, Peopl. Rep. China, Huaxue Yu Nianhe, 4:208–11 (1992).

S.J. Gregg and K.S.W. Sing in "Adsorption, Surface Area, and Porosity", Academic Press Inc., 2nd Ed., London (1982) pp. 41–105.

"Practical Refractometry by Means of a Microscope" Roy M. Allen, $2^{nd}$ Edition, Cargille, NJ pp. 6–7.

(List continued on next page.)

*Primary Examiner*—Peter Szekely
(74) *Attorney, Agent, or Firm*—Steven E. Skolnick

(57) ABSTRACT

Polymerizable composition that include: (a) a cationically active functional group; (b) an initiation system capable of initiating cationic polymerization of the cationically active functional group; and (c) a filler composition that includes various radiopacifying fillers in an amount sufficient to render the polymerizable composition radiopaque. Components (a), (b), and (c) are selected such that the polymerizable composition polymerizes to form a polymerized composition having a Barcol hardness, measured using a GYZJ-935 meter, of at least 10 within 30 minutes following initiation of the cationically active functional group are a reaction temperature of 25° C.

10 Claims, 9 Drawing Sheets

U.S. PATENT DOCUMENTS

| | | | |
|---|---|---|---|
| 4,617,279 A | 10/1986 | Manabe et al. | 501/210 |
| RE32,299 E | 12/1986 | Randklev | 501/59 |
| 4,642,126 A | 2/1987 | Zador et al. | 51/295 |
| 4,652,274 A | 3/1987 | Boettcher et al. | 51/298 |
| 4,694,029 A | 9/1987 | Land | 522/8 |
| 4,719,149 A | 1/1988 | Aasen et al. | 428/473 |
| 4,751,138 A | 6/1988 | Tumey et al. | 428/323 |
| 4,771,112 A | 9/1988 | Engelbrecht | 525/327.3 |
| 4,772,511 A | 9/1988 | Wood et al. | 428/325 |
| 4,774,267 A * | 9/1988 | Weintraub | 523/117 |
| 4,831,066 A * | 5/1989 | Weintraub | 523/117 |
| 4,839,401 A | 6/1989 | Waknine | 522/14 |
| 4,920,082 A | 4/1990 | Danielson | 501/59 |
| 4,985,340 A | 1/1991 | Palazzotto et al. | 430/270 |
| 5,078,753 A | 1/1992 | Broberg et al. | 51/298 |
| 5,095,045 A | 3/1992 | Winkel et al. | 523/115 |
| 5,204,398 A | 4/1993 | Cohen et al. | 523/116 |
| 5,256,170 A | 10/1993 | Harmer et al. | 51/293 |
| 5,266,609 A | 11/1993 | Hall et al. | 523/116 |
| 5,318,999 A | 6/1994 | Mitra et al. | 522/57 |
| 5,413,971 A | 5/1995 | McPherson | 501/78 |
| 5,426,134 A | 6/1995 | Rheinbergern et al. | 523/118 |
| 5,436,063 A | 7/1995 | Follett et al. | 428/224 |
| 5,453,450 A | 9/1995 | Kinzer et al. | 522/18 |
| 5,472,991 A | 12/1995 | Schmitt et al. | 522/4 |
| 5,545,676 A | 8/1996 | Palazzotto et al. | 522/15 |
| 5,565,011 A | 10/1996 | Follett et al. | 51/297 |
| 5,571,297 A | 11/1996 | Swei et al. | 51/298 |
| 5,582,672 A | 12/1996 | Follett et al. | 156/279 |
| 5,599,622 A | 2/1997 | Kinzer et al. | 428/355 |
| 5,624,976 A | 4/1997 | Klee | 523/116 |
| 5,672,637 A | 9/1997 | Mahoney et al. | 522/25 |
| 5,721,289 A | 2/1998 | Karim et al. | 522/31 |
| 5,808,108 A | 9/1998 | Chappelow et al. | 549/335 |
| 5,808,128 A * | 9/1998 | Chappelew et al. | 523/116 |
| 5,856,373 A * | 1/1999 | Kaisaki et al. | 523/117 |
| 6,043,295 A * | 3/2000 | Oxman et al. | 523/117 |
| 6,057,460 A * | 5/2000 | Moszner et al. | 549/463 |
| 6,084,004 A * | 7/2000 | Weinmann et al. | 522/25 |
| 6,147,136 A * | 11/2000 | Bissinger | 523/116 |
| 6,187,833 B1 * | 2/2001 | Oxman et al. | 523/117 |
| 6,245,828 B1 * | 6/2001 | Weinmann et al. | 523/116 |

OTHER PUBLICATIONS

Tang et al., "Study of Diisocyanate Modified EAM Resin for Orthodontics Adhesive," *Stonatol. Coll., 4 hu th Mil. Med. Univ.,* Peopl. Rep. of China, Huaxue Yu Nianhe, 4:208–11 (1992).

Moore et al., "Free Radical and Cationic Cure of Pigmented Coatings Using Visible Light Photoinitiators," Spectra Group Ltd., p. 17–24.

Hans et al., "Photoinitiator Systems for Concurrent Radical and Cationic Polymerization," *Pure & Appt. Chem.,* 60(7):1033–1038 (1988).

Wang et al., "Photopolymerization of Glycidyl Acrylate and Glycidyl Methacrylate Investigated by Differential Photocalorimetry and FT–I.R.," *Eur. Poly. J.,* 29(10):1379–1386 (1993).

Lee et al., "Properties of a New Carvable Composite Dental Filling Material," *Australian Dental Journal,* 22(4):232–235 (1977).

Timpe et al., "Bivalent Initiators—Novel Systems for the Photopolymerization," *Sci. Journ. Techn. Univer. Leuna–Merseburg,* 26(3):439–449 (1984).

Phillips, "composite Restorative Resins," *JADA* 80:357–358 (1970).

Ferrancane, "Current Trends in Dental Composites," *Crit. Rev. Oral Biol. Med.,* 6(4):302–318 (1995).

* cited by examiner

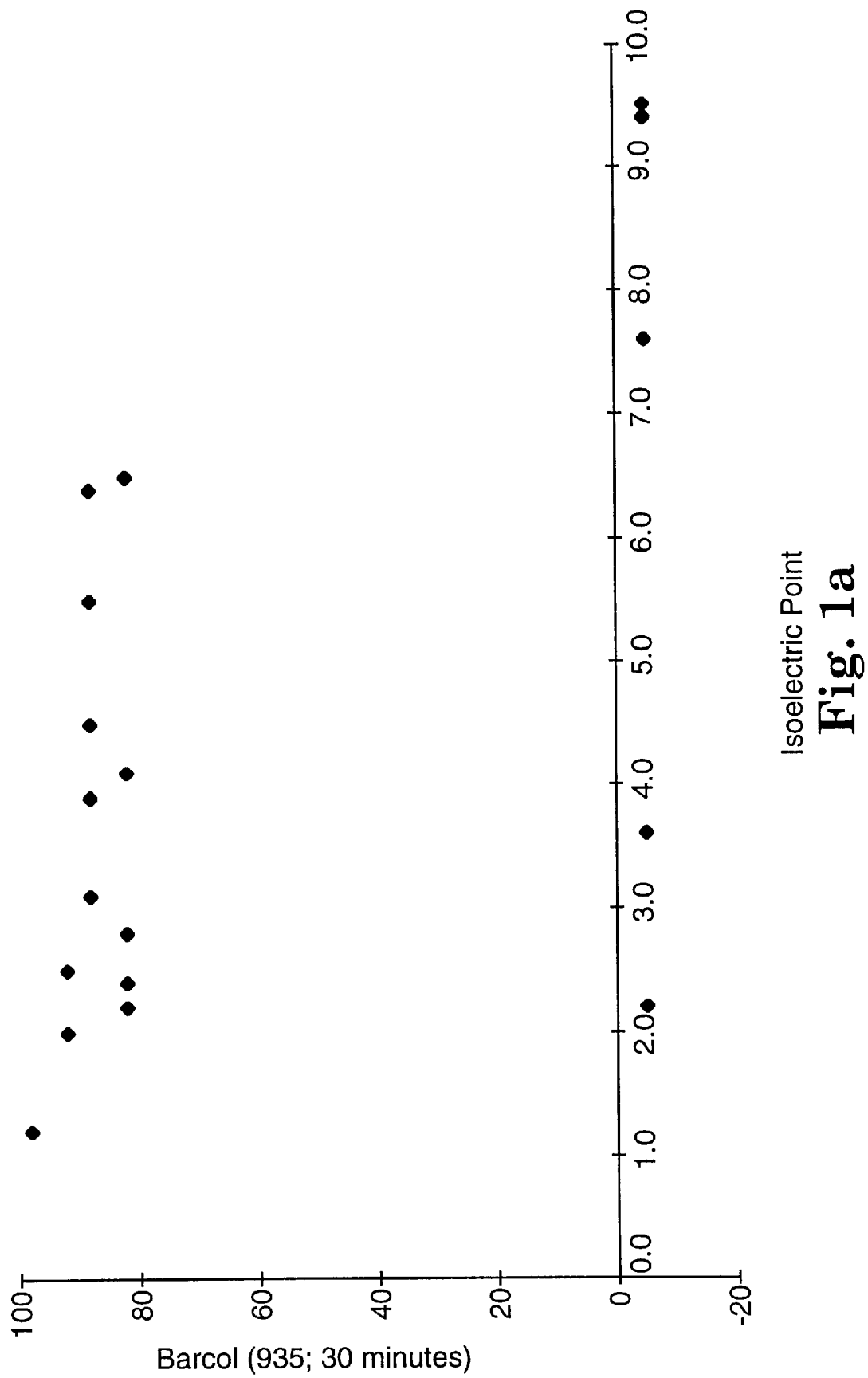

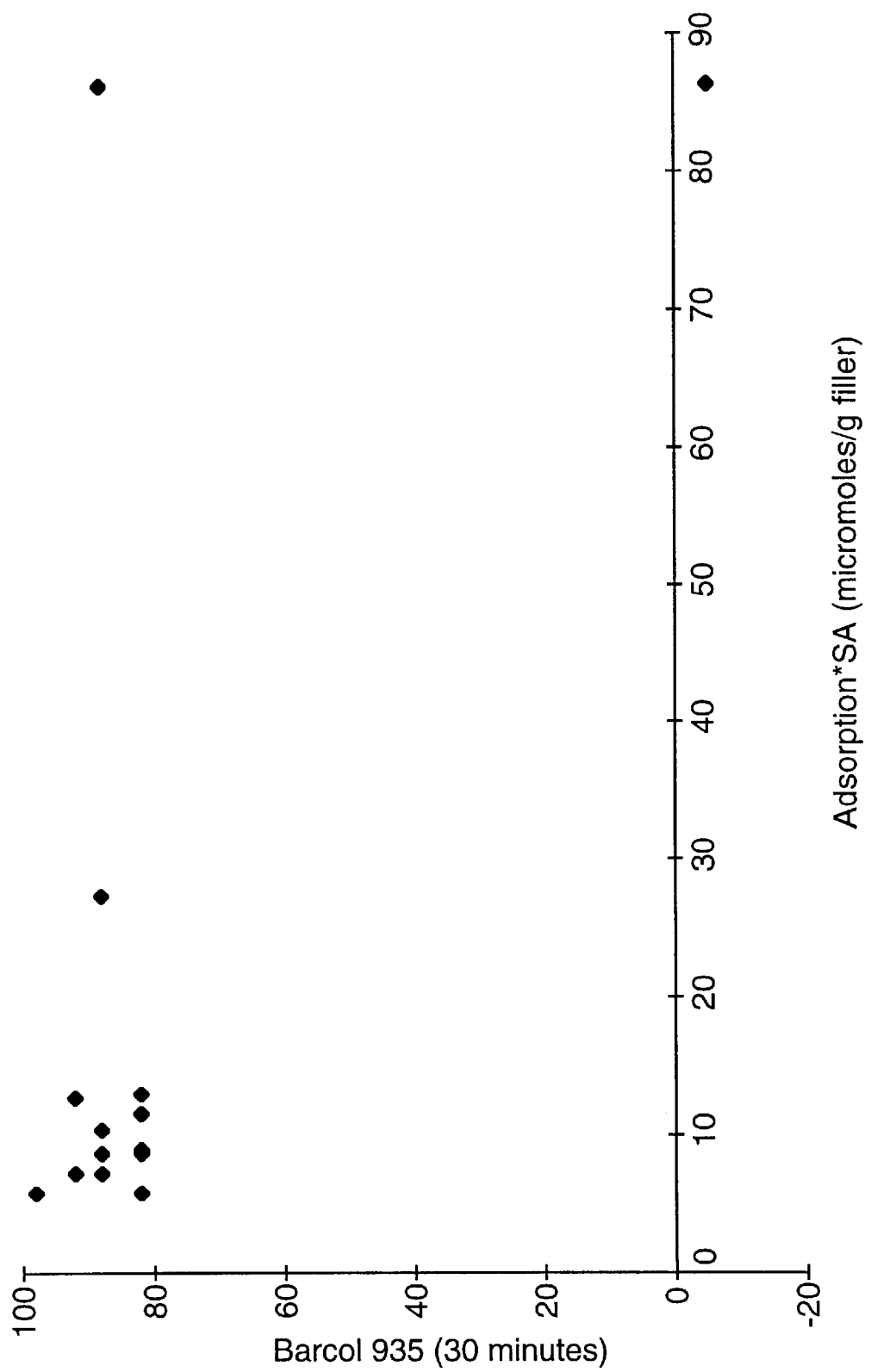

RADIOPAQUE CATIONICALLY POLYMERIZABLE COMPOSITIONS COMPRISING A RADIOPACIFYING FILLER, AND METHOD FOR POLYMERIZING SAME

This is a divisional of application Ser. No. 09/168,051 filed Oct. 7, 1998, now U.S. Pat. No. 6,306,926.

BACKGROUND OF THE INVENTION

The invention relates to polymerizing radiopaque compositions that include cationically active functional groups and radiopacifying fillers.

Fillers are often added to polymer resins to form composites having higher strength values than the polymer resin itself. Dental composites, for example, typically feature high filler loadings on the order of 50% by weight or higher.

Non-radiopacifying fillers such as quartz and silica have been successfully combined with free radically polymerizable components such as acrylates and methacrylates and a free radical initiator to form a useful dental composite following exposure to polymerization conditions. Such fillers also have been successfully used with cationically polymerizable components such as epoxy resins and a cationic initiator to form useful dental composites following cationic-initiated polymerization.

In many instances it is desirable to use a radiopacifying filler to create a radiopaque composite. Such composites are particularly useful in dental applications because the composite is x-ray detectable. Radiopacifying fillers have been successfully combined with free radically polymerizable components and free radical initiators to form dental composites. It would also be desirable to combine radiopacifying fillers with cationic initiators and cationically polymerizable components such as epoxy resins which undergo less shrinkage than acrylates and methacrylates upon polymerization.

SUMMARY OF THE INVENTION

Although there is a need for a radiopaque composite prepared by combining a cationic initiator, a cationically polymerizable component and a radiopacifying filler, the inventors have discovered that, unlike free radically polymerizable systems, not all polymerizable resin-filler-initiator combinations will produce a useful composite (i.e., a radiopaque composite having a Barcol hardness of at least 10 measured using a GYZJ-935 meter) upon exposure to polymerization conditions. In many cases, the inventors have discovered, the radiopacifying filler inhibits or suppresses the cationic polymerization mechanism. In some cases, the net result is a composite having a hardness value lower than the hardness value of the unfilled resin.

The inventors have now discovered that certain radiopacifying fillers, when combined with cationic initiators and cationically polymerizable components, will produce composites having a Barcol hardness of at least 10 (measured using the GYZJ-935 meter) following exposure to polymerization conditions. In some cases, this requires treating fillers that would otherwise interfere with the cationic polymerization mechanism, e.g., by heating or coating the fillers. The inventors have further identified selection criteria that can be used to screen cationic initiator-resin-radiopacifying filler combinations. The inventors have thus made it possible to prepare useful composites based upon cationic initiators, cationically polymerizable resins, and radiopacifying fillers.

Accordingly, the invention features, in a first aspect, a polymerizable composition that includes:

(a) a cationically active functional group;
(b) an initiation system capable of initiating cationic polymerization of the cationically active functional group; and
(c) a filler composition comprising a radiopacifying filler in an amount sufficient to render the polymerizable composition radiopaque. The radiopacifying filler is selected from the group consisting of metal oxides, metal halides, metal borates, metal phosphates, metal silicates, metal carbonates, metal germanates, metal tetrafluoroborates, metal hexafluorophosphates, and combinations thereof. The combinations may be in the form of physical blends or chemical compounds.

Components (a), (b), and (c) are selected such that the polymerizable composition polymerizes to form a polymerized composition having a Barcol hardness, measured according to Test Procedure A, infra, using a GYZJ-935 meter, of at least 10 within 30 minutes following initiation of the cationically active functional group at a reaction temperature of 25 C. Initiation can be determined using differential scanning calorimetry, and is manifested as an increase in enthalpy.

As used herein, a "radiopaque composition" is a composition that has the ability to diminish the path of x-rays to the same extent as an aluminum sample having the same thickness such that the density of an x-ray image of the composition is less than the density of the x-ray image of the aluminum, determined according to Procedure 7.11 of International Standard IS04049; 1988(E), "Dentistry—Resin-Based Filling Materials."

A "cationically active functional group" is a chemical moiety that is activated in the presence of an initiator capable of initiating cationic polymerization such that it is available for reaction with other compounds bearing cationically active functional groups.

A "free radically active functional group" is a chemical moiety that is activated in the presence of an initiator capable of initiating free radical polymerization such that it is available for reaction with other compounds bearing free radically active functional groups.

A "metal oxide" is a compound that contains only a metal and oxygen.

A "metal halide" is a compound that contains, at a minimum, a metal and a halogen (e.g., chlorine, bromine, iodine, or fluorine).

A "metal borate" is a compound that contains, at a minimum, a metal, boron, and oxygen.

A "metal phosphate" is a compound that contains, at a minimum, a metal, phosphorous, and oxygen.

A "metal silicate" is a compound that contains, at a minimum, a metal, silicon, and oxygen. Thus, for example, a metal aluminosilicate containing a metal, aluminum, silicon, and oxygen would be considered a "metal silicate" for the purposes of this invention.

A "metal carbonate" is a compound that contains, at a minimum, a metal and a $CO_3$ group.

A "metal germanate" is a compound that contains, at a minimum, a metal, germanium, and oxygen.

A "metal tetrafluoroborate" is a compound that contains only a metal and a $BF_4$ group.

A "metal hexafluorophosphate" is a compound that contains only a metal and a $PF_6$ group.

The composition may also include a free radically polymerizable component such as an acrylic or methacrylic acid ester. Such compositions are often referred to as "hybrid" compositions. In a hybrid composition, free radical polymerization of the free radically active functional groups assists in obtaining the requisite Barcol hardness value of the composite. Nevertheless, even in hybrid compositions it is cationic polymerization of the cationically active functional group that preferably forms a polymerized composition having the requisite hardness value under the polymerization conditions described above.

In some embodiments, the polymerizable composition polymerizes to form a polymerized composition have a Barcol hardness, measured using a GYZJ-934-1 meter according to Test Procedure A, infra, of at least 10 within 30 minutes following initiation of the cationically active group.

The inventors have identified several screening tests for use in designing successful polymerizable compositions. Preferably, these tests are used in combination with each other.

One test focuses on the radiopacifying fillers themselves and is based upon isoelectric point measurements. The isoelectric point of any particular radiopacifying filler is independent of filler loading. However, the filler loading influences which values of isoelectric point are required in order to result in a successful cationic polymerization. According to this test, therefore, the filler composition is selected such that when the amount of the radiopacifying filler is at least 50% by weight of the polymerizable composition, the radiopacifying filler has an isoelectric point, measured according to Test Procedure B, infra, of no greater than 7.

Other tests focus on the interaction between the radiopacifying filler and a test polymerizable composition that includes a cationically polymerizable component and a cationic initiator. According to one such test, the filler composition is selected such that when the amount of the filler composition is 70% by weight of the polymerizable composition, a test polymerizable composition defined in Test Procedure C, infra, that includes the filler composition has an adsorption value of no greater than 20 micromoles/g filler, as determined by surface area titration according to Test Procedure C. When the amount of the filler composition is 50% by weight of the polymerizable composition, the adsorption value is no greater than 80 micromoles/g filler.

According to another test, the filler composition is selected such that when the amount of the filler composition is 70% by weight of the polymerizable composition, the filler composition causes a change in conductivity of a test solution of no greater than 60 mV, determined according to Test Procedure D, infra. When the amount of the filler composition is 50% by weight of the polymerizable composition, the change in conductivity is no greater than 125 mV.

The selection criteria are phrased in terms of certain filler loadings. However, it should be understood that the particular filler loading is provided as a test. Accordingly, polymerizable compositions having filler loadings different from the loadings associated with the selection criteria are within the scope of the invention provided that, for any particular filler/resin/initiator combination, if the filler loading were the same as the amount recited in the selection criteria, the requirements of those criteria would be met.

Both the chemical composition and physical form of the radiopacifying filler, including its surface characteristics, as well as the process used to prepared the filler, are variables which influence the effect of the filler on the cationic polymerization mechanism for a given polymerizable resin-filler-initiator combination. Sol-gel-derived, melt-derived, vapor-derived, and mineral radiopacifying fillers can be used. The radiopacifying filler may also be in the form of one or more inorganic radiopacifying particles dispersed in a polymer matrix. In the case of sol-gel-derived fillers, the filler composition is selected such that the filler composition has a relative peak height of greater than 80% as determined by Fourier transform infrared spectroscopy according to Test Procedure E, infra.

Semi-crystalline and amorphous microstructures are generally preferred. An "amorphous" filler is one which does not give rise to a discernible x-ray powder diffraction pattern. A "semi-crystalline" filler is one which gives rise to a discernible x-ray powder diffraction pattern.

With respect to chemical composition, the radiopacifying filler preferably includes an element having an atomic number of at least 30. Examples include yttrium, strontium, barium, zirconium, hafilium, niobium, tantalum, tungsten, molybdenum, tin, zinc, lanthanide elements (i.e., elements having atomic numbers ranging from 57 to 71, inclusive), and combinations thereof. Particularly preferred are radiopacifying fillers that include: (a) an oxide selected from the group consisting of lanthanum oxide, zinc oxide, tantalum oxide, tin oxide, zirconium oxide, yttrium oxide, ytterbium oxide, barium oxide, strontium oxide, and combinations thereof, combined with (b) an oxide selected from the group consisting of aluminum oxide, boron oxide, silicon oxide, and combinations thereof. Specific examples of suitable radiopacifying fillers include the following:

(a) Fillers that include 0.5% to 55% by weight lanthanum oxide and 45% to 99% by weight silicon oxide. The fillers preferably have a semi-crystalline or amorphous microstructure. In terms of processing, the fillers are preferably sol-gel- or melt-derived.

(b) Fillers that include 0.5% to 55% by weight lanthanum oxide, 0.5% to 50% by weight aluminum oxide, and 0.5% to 90% by weight silicon oxide. The fillers preferably have a semi-crystalline or amorphous microstructure. In terms of processing, the fillers ar preferably sol-gel- or melt-derived.

(c) Fillers that include 0.5% to 55% by weight lanthanum oxide, 0.1% to 55% by weight aluminum oxide, 0.01% to 80% by weight boron oxide, and 1% to 90% by weight silicon oxide. The fillers preferably have an amorphous microstructure. In terms of processing, the fillers are preferably sol-gel- or melt-derived.

(d) Fillers that include 0.5% to 55% by weight lanthanum oxide, 0.01% to 80% by weight boron oxide, and 1% to 90% by weight silicon oxide. The fillers preferably have a semi-crystalline or amorphous microstructure. In terms of processing, the fillers are preferably sol-gel- or melt-derived.

(e) Fillers that include 0.5% to 55% by weight zinc oxide, 0.5% to 55% by weight lanthanum oxide, 0.1% to 40% by weight aluminum oxide, 0.01% to 80% by weight boron oxide, and 1% to 80% by weight silicon oxide. The fillers preferably have an amorphous microstructure. In terms of processing, the fillers are preferably melt-derived.

(f) Fillers that include colloidally derived zirconium oxide.

(g) Fillers that include 0.5% to 55% by weight zirconium oxide and 45% to 99% by weight silicon oxide. The fillers preferably have a semi-crystalline or amorphous microstructure. In terms of processing, the fillers are preferably sol-gel-derived.

(h) Fillers that include 0.5% to 55% by weight zirconium oxide, 0.01% to 40% by weight boron oxide, and 1% to 90% by weight silicon oxide. The fillers preferably have a semi-crystalline or amorphous microstructure. In terms of processing, the fillers are preferably sol-gel-derived.

(i) Fillers that include 0.5% to 55% by weight yttrium oxide and 1% to 90% by weight silicon oxide. The fillers preferably have a semi-crystalline or amorphous microstructure. In terms of processing, the fillers are preferably derived from a sol-gel. The fillers preferably have a semi-crystalline or amorphous microstructure. In terms of processing, the fillers are preferably sol-gel-derived.

(j) Fillers that include 0.5% to 55% by weight yttrium oxide, 0.1% to 50% by weight aluminum oxide, and 1% to 90% by weight silicon oxide. The fillers preferably have a semi-crystalline or amorphous microstructure. In terms of processing, the fillers are preferably sol-gel- or melt-derived.

(k) Fillers that include 0.5% to 55% by weight barium oxide, 0.1% to 40% by weight aluminum oxide, 0.01% to 80% by weight boron oxide, and 1% to 90% silicon oxide. The filler preferably has an amorphous microstructure. In terms of processing, the fillers are preferably is melt-derived.

(l) Fillers that include 0.5% to 55% by weight strontium oxide, 0.1% to 40% by weight aluminum oxide, 0.01% to 80% by weight boron oxide, and 1% to 90% by weight silicon oxide. The filler preferably has an amorphous microstructure. In terms of processing, the fillers are preferably derived from a melt.

(m) Fillers that include a fluoride such as a lanthanide fluoride (e.g., ytterbium fluoride), yttrium fluoride, zinc fluoride, tin fluoride, and combinations thereof.

In some cases, the above-described radiopacifying fillers may be used "as is." In other cases, it is necessary to treat the fillers, e.g., by heat treating the fillers or by coating them. Accordingly, even fillers which do not meet the above-described selection criteria initially can be used successfully if treated properly.

The coated radiopacifying fillers include a core having a first chemical composition and a coating (which may or may not be continuous) on the surface of the core having a second chemical composition different from the first chemical composition. Examples of useful core materials include quartz, fused quartz, silicate glass (including borosilicate glass), zirconium oxide-silicon oxide, zirconium oxide-boron oxide-silicon oxide, and combinations thereof. Examples of useful coatings include silicate glass (including borosilicate glass), boron oxide, colloidally derived silicon oxide, colloidally derived zirconium oxide, and combinations thereof. Polymer coatings can also be used. In some cases, the coating offers the additional advantages of reducing shrinkage upon polymerization and opacity. The reduced opacity, in turn, enhances the ability to obtain good depth of cure in photopolymerizable compositions. The coating may also provide anchorage for, e.g., silane treatments.

The amount of filler composition preferably is at least 50% by weight, and more preferably at least 70% by weight, based upon the total weight of the polymerizable composition. In addition to the radiopacifying filler, the filler may include non-radiopacifying fillers such as quartz, calcium carbonate, feldspar, $KBF_4$, cryolite, and combinations thereof.

The initiator system is preferably a photoinitiator system. Photoinitiated compositions preferably polymerize to form a polymerized composition having a depth of cure of at least 2 mm, preferably at least 6 mm, and more preferably at least 8 mm within 30 minutes following initiation of the cationically active functional group at a reaction temperature of 37° C. Useful initiator systems include onium salts such as iodonium and sulfonium salts, and organometallic complex salts.

Examples of suitable materials having cationically active functional groups include epoxy resins, vinyl ethers, spiro ortho esters, spiro ortho carbonates, bicylic ortho esters, bicyclic monolactones, bicyclic bislactones, cyclic carbonates, and combinations thereof. Such materials can be used alone or combined with reactants having free radically active functional groups to form hybrid compositions. It is also possible to include reactants that contain both free radically active functional groups and cationically active functional groups in a single molecule.

In the case of hybrid compositions, the composition may include a separate initiator system capable of initiating free radical polymerization of the free radically active functional group. Alternatively, the composition may include a single initiator system capable of initiating both free radical and cationic polymerization.

Examples of useful polymerizable compositions include dental composites, orthodontic bracket adhesives, and orthodontic band cements. As used herein, the term "composite" refers to a filled dental material. The term "restorative" refers to a composite which is polymerized after it is disposed adjacent to a tooth. The term "prosthesis" refers to a composite which is polymerized for its final use (e.g., as crown, bridge, veneer, inlay, onlay or the like) before it is disposed adjacent to a tooth. The term "sealant" refers to a lightly filled composite which is polymerized after it is disposed adjacent to a tooth. Each of these materials is suitable for temporary or permanent use.

In a second aspect, the invention features a photopolymerizable dental composite that includes:

(a) a cationically active functional group;

(b) a photoinitiation system capable of initiating cationic polymerization of the cationically active functional group upon exposure to visible light; and (c) a filler composition comprising a radiopacifying filler in an amount sufficient to render the polymerizable composition radiopaque. Upon exposure to visible light, the composite polymerizes to form a polymerized dental composite having a Barcol hardness, measured according to Test Procedure A, infra using a GYZJ-935 meter, of at least 10 within 30 minutes following initiation of the cationically active functional group at a reaction temperature of 25° C. The composite may further include an ethylenically unsaturated reactant, as described above.

Preferably, the resulting composite has a Barcol hardness, measured using a GYZJ-934-1 meter according to Test Procedure A, of at least 10 within 30 minutes following initiation of the cationically active functional group at a reaction temperature of 25° C. The amount of filler in the composite preferably is at least 50% by weight based upon the total weight of the polymerizable composite. The composite preferably polymerizes to form a polymerized composite having a depth of cure of at least 2 mm within 30 minutes following initiation of the cationically active functional group at a reaction temperature of 37° C.

In a third aspect, the invention features a polymerizable composition that includes:

(a) a cationically active functional group;

(b) an initiation system capable of initiating cationic polymerization of the cationically active functional group; and (c) a filler composition comprising a radiopacifying filler other than a sulfate in an amount sufficient to render the polymerizable composition radiopaque. Components (a), (b), and (c) are selected such that the polymerizable composition polymerizes to form a polymerized composition having a Barcol hardness, measured according to Test Procedure A, infra, using a GYZJ-935 meter, of at least 10 within 30 minutes following initiation of the cationically active functional group at a reaction temperature of 25° C.

In a fourth aspect, the invention features a method of preparing a polymerized composition that includes:
(a) providing a polymerizable composition that includes (i) a cationically active functional group; (ii) an initiation system capable of initiating cationic polymerization of the cationically active functional group; and (iii) a filler composition that includes a radiopacifying filler in an amount sufficient to render the composition radiopaque; and
(b) initiating polymerization of said cationically active functional group to form said polymerized composition, preferably at a reaction temperature of 37° C. or less. The radiopacifying filler is selected from the group consisting of metal oxides, metal halides, metal borates, metal phosphates, metal silicates, metal carbonates, metal germanates, metal tetrafluoroborates, metal hexafluorophosphates, and combinations thereof, where these terms have the meanings set forth above. The polymerizable composition is selected such that it is capable of polymerizing to form a polymerized composition having a Barcol hardness, measured according to Test Procedure A, infra, using a GYZJ-935 meter, of at least 10 within 30 minutes following initiation of the cationically active functional group at a reaction temperature of 25° C. Examples of useful polymerized products include dental composites.

In one embodiment, the initiation system is a photoinitiation system, in which case the method includes exposing the polymerizable composition to actinic radiation to initiate polymerization of the cationically active functional group. Preferably, the initiation system includes a visible light sensitizer as well such that polymerization is initiated by exposing the composition to visible light. Other suitable sources of actinic radiation include sources of ultraviolet radiation. Thermal initiation systems may also be used, in which case the method includes exposing the composition to thermal radiation to initiate polymerization of the cationically active functional group.

The inventors have further discovered a number of novel fillers. Such fillers are useful in both free radically polymerizable compositions, cationically polymerizable compositions, and hybrid compositions featuring both free radically and cationically polymerizable components. Some of these fillers have high clarity and form composites having relatively low opacity with respect to visible light. Some of these fillers also exhibit low surface area and low residual porosity.

One filler is a melt-derived filler that includes 5–25% by weight aluminum oxide, 10–35% by weight boron oxide, 15–50% by weight lanthanum oxide, and 20–50% by weight silicon oxide.

Another filler is a melt-derived filler that includes 10–30% by weight aluminum oxide, 10–40% by weight boron oxide, 20–50% by weight silicon oxide, and 15–40% by weight tantalum oxide.

A third filler is a melt-derived filler that includes 5–30% by weight aluminum oxide, 5–40% by weight boron oxide, 0–15% by weight lanthanum oxide, 25–55% by weight silicon oxide, and 10–40% by weight zinc oxide.

A fourth filler is a melt-derived filler that includes 15–30% by weight aluminum oxide, 15–30% by weight boron oxide, 20–50% by weight silicon oxide, and 15–40% by weight ytterbium oxide.

A fifth filler is in the form of non vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound. The microparticles are substantially free of crystalline microregions or inhomogeneities detectable via powder x-ray diffraction. A sixth filler is in the form of non vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound. The microparticles include: (i) a plurality of amorphous microregions comprising oxygen and silicon, (ii) a plurality of radiopacifying, semicrystalline, metal oxide microregions, and (iii) no greater than about 40% by weight of $B_2O_3$ or $P_2O_5$. The amorphous microregions are substantially uniformly interspersed with the semicrystalline microregions. In addition, the microparticles are substantially free of crystalline microregions or inhomogeneities having diameters greater than 0.4 micrometers.

Other features and advantages of the invention will be apparent from the following description of preferred embodiments thereof, and from the claims.

BRIEF DESCRIPTION OF THE DRAWINGS

FIGS. 1(a) and 1(b) are plots of Barcol hardness (GYZJ-935 at minutes post-illumination) vs. isoelectric point, measured according to Test Procedure B, for composites having filler loadings of 50 and 70% (w/w/), respectively.

FIGS. 2(a) and 2(b) are plots of Barcol hardness (GYZJ-935 at 30 minutes post-illumination) vs. adsorption values, measured according to Test Procedure C, for composites having filler loadings of 50 and 70% (w/w), respectively.

DETAILED DESCRIPTION

Figure 1B:
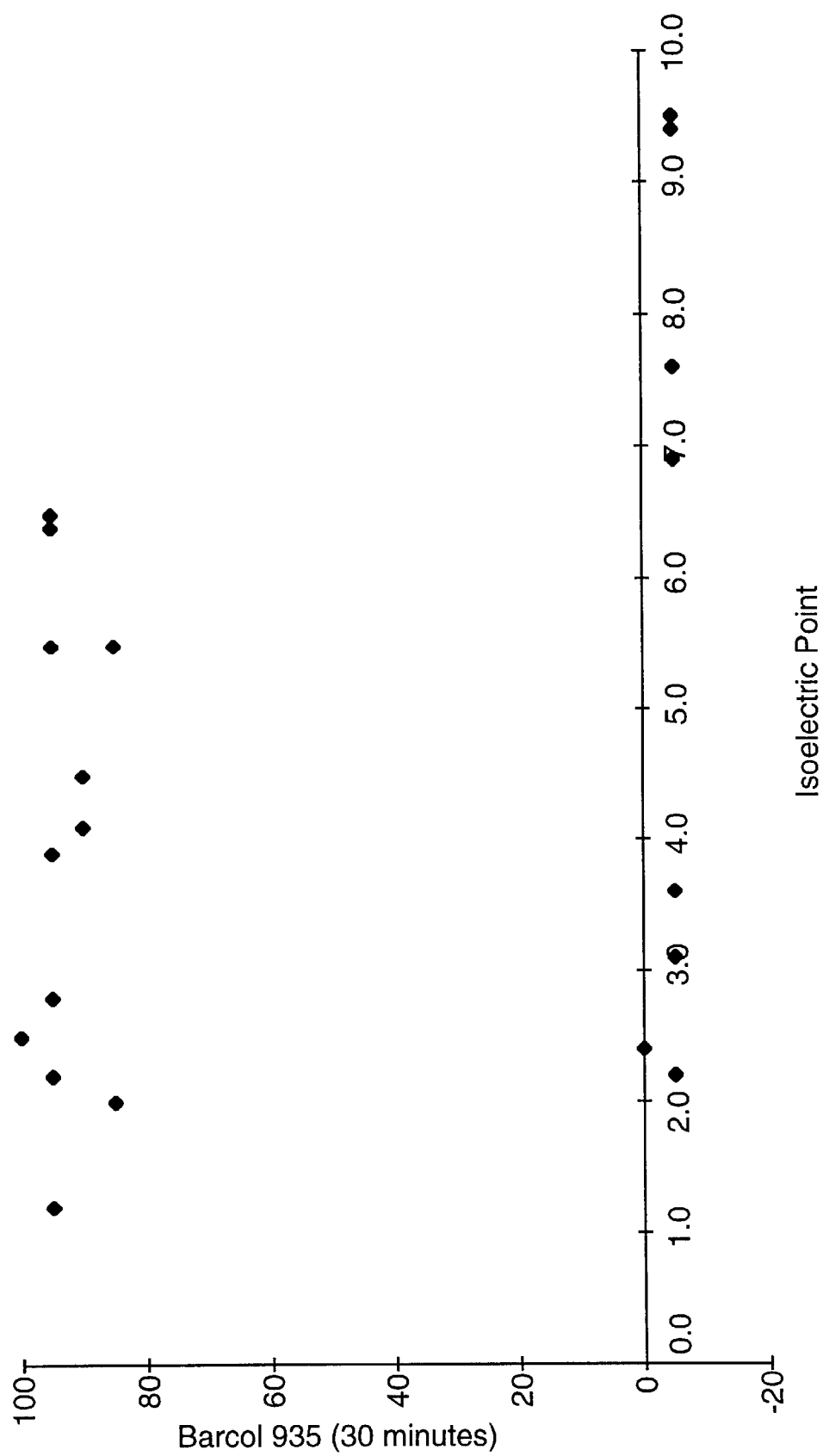

The invention provides filled, radiopaque, cationically polymerizable compositions that undergo cationically initiated polymerization to form useful composites. Free radically polymerizable reactants and initiators may be included as well. The compositions are particularly suitable for dental applications. The inventors have discovered that by carefully selecting the individual components of the composition, including the initiator, polymerizable components, and radiopacifying filler, the problem of the filler inhibiting or suppressing cationic polymerization, and thereby preventing formation of a suitably hard composite, can be avoided. The selection process involves using the screening tests identified in the Summary of the Invention, above, to design appropriate filler-polymerizable resin-initiator combinations. For best results, the tests should be used in conjunction with each other.

The individual components of the polymerizable composition will now be described.

Filler Composition

The filler composition preferably forms at least 50% by weight, and more preferably at least 70% by weight, of the polymerizable composition. Lower filler loadings, however, may be used as well. It includes at least one radiopacifying filler. The amount of radiopacifying filler is sufficient to render the polymerizable composition radiopaque. Suitable radiopacifying fillers are described in the Summary of the Invention, above. Preferably, the fillers have a semi-crystalline or amorphous microstructure.

Commercially available sources of radiopacifying fillers are described in the Examples, infra. Alternatively, the radiopacifying fillers may be synthesized using ceramic processing techniques including sol-gel processing, melt processing, vapor phase processing, and colloidal processing.

In some instances, a particular radiopacifying filler that does not satisfy the above-identified screening tests can be treated such that the resulting filler composition then passes one or more of these tests. The treatment modifies the surface characteristics of the filler and thus its interaction with the other components of the polymerizable composition. For example, heat-treating the filler can convert a seemingly unusable radiopacifying filler into a useful filler. The particular heat-treatment temperature is a function of the individual filler. In general, however, heat-treatment temperatures for both melt-derived and sol-gel-derived fillers are on the order of about 400° C. or higher.

Another treatment protocol involves coating the filler particles with one or more materials having a composition different from that of the core filler. Examples of suitable coatings include low temperature melting amorphous materials applied in the form of sols (e.g., colloidal sols such as colloidal zirconium oxide sols) and then optionally fired, polymers, and polymerizable monomers. Suitable coating techniques include spray drying, magnetic coating, tray drying, vapor coating, flame spraying, electrostatic spraying, fluidized bed processes, and sol-gel processes.

Other examples of useful treatment protocols which can be used to alter the surface characteristics of the radiopacifying filler include wet milling (in the case of glass fillers), grinding, and the incorporation of fluxing agents such as boron oxide during filler preparation.

The filler composition may also include non-radiopacifying fillers. Examples include quartz, fused quartz, fumed silica, calcium carbonate, feldspar, $KBF_4$, cryolite, and combinations thereof.

Initiation System

One class of useful initiators includes sources of species capable of initiating both free radical and cationic polymerization. Representative examples include onium salts and mixed ligand arene cyclopentadienyl metal salts with complex metal halide ions, as described in "CRC Handbook of Organic Photochemistry", vol II, ed. J. C. Scaiano, pp. 335–339 (1989). Preferably, the source is an onium salt such as a sulfonium or iodonium salt. Of the onium salts, iodonium salts (e.g., aryl iodonium salts) are particularly useful. The iodonium salt should be soluble in the composition and preferably is shelf-stable, meaning it does not spontaneously promote polymerization when dissolved therein in the presence of the cationic polymerization modifier and photosensitizer (if included). Accordingly, selection of a particular iodonium salt may depend to some extent upon the particular polymerizable reactants, cationic polymerization modifiers, and sensitizers (if present).

Suitable iodonium salts are described in U.S. Pat. Nos. 3,729,313; 3,741,769; 4,250,053; and 4,394,403, the iodonium salt disclosures of which are incorporated herein by reference. The iodonium salt can be a simple salt, containing an anion such as $Cl^-$, $Br^-$, $I^-$, $C_4H_5SO_3^-$, or $C(SO_2CF_3)_3^{3-}$; or a metal complex salt containing an antimonate, arsenate, phosphate, or borate such as $SbF_5OH^-$, $AsF_6^-$, or $B(C_6F_5)_4^-$. Mixtures of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; diphenyliodonium hexafluoroantimonate; diphenyl or diaryliodonium tris-trifluoromethlylsulfonyl methide; or diphenyl or diaryliodonium tetra(pentafluorophenyl)borate.

The initiation system may also include a sensitizer such as a visible light sensitizer that is soluble in the polymerizable composition. The sensitizer preferably is capable of absorbing light having wavelengths in the range from about 300 to about 1000 nanometers.

Examples of suitable sensitizers include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. For applications requiring deep cure (e.g., cure of highly filled composites), it is preferred to employ sensitizers having an extinction coefficient below about 100 $lmole^{-1}cm^{-1}$, more preferably about or below 100 $lmole^{-1}cm^{-1}$, at the desired wavelength of irradiation for photopolymerization. The alpha-diketones are an example of a class of sensitizers having this property, and are particularly preferred for dental applications.

Examples of particularly preferred visible light sensitizers include camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione; Of these, camphorquinone is the most preferred sensitizer.

In some cases it may be desirable to delay the onset of cationic polymerization. For example, in the case of a hybrid composition that includes both free radically active functional groups and cationically active functional groups, it may be desirable to use an initiation system suitable for initiating both free radical and cationic polymerization which is designed such that for a given reaction temperature, photoinitiation of free radical polymerization occurs after a finite induction period $T_1$ and photoinitiation of cationic polymerization occurs after a finite induction period $T_3$, where $T_3$ is greater than $T_1$. $T_1$ and $T_3$ are measured relative to administration of the first dose of actinic radiation which occurs at $T_0$. Such initiation systems are described in Oxman et al., "Compositions Featuring Cationically Active and Free Radically Active Functional Groups, and Methods for Polymerizing Such Compositions," U.S. Pat. No. 6,187,836, which is assigned to the same assignee as the present application and hereby incorporated by reference. As described therein, the photoinitiation system includes: (i) a source of species capable of initiating free radical polymerization of the free radically active functional group and cationic polymerization of the cationically active functional group; and (ii) a cationic polymerization modifier. The amount and type of modifier are selected such that in the absence of the modifier, initiation of cationic polymerization under the same irradiation conditions occurs at the end of a finite induction period $T_2$ (also measured relative to $T_0$), where $T_2$ is less than $T_3$.

The induction periods ($T_1$, $T_2$, and $T_3$) can be measured using differential scanning calorimetry. Following the first irradiation event at $T_0$, the enthalpy of the reaction is measured as a function of time. Both initiation of free radical polymerization and initiation of cationic polymerization result in an increase in enthalpy, observed as a pair of separate peaks on the graph. The time at which initiation occurs is taken to be the time at which the enthalpy begins to rise.

The cationic polymerization modifier preferably has a photoinduced potential less than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone, measured according to the procedure described in the aforementioned Oxman et al. application. In general, useful cationic polymerization modifiers are typically bases having $pK_b$ values, measured in aqueous solution, of less than 10. Examples of classes of suitable cationic polymerization modifiers include aromatic amines, aliphatic amines, aliphatic amides, aliphatic ureas; aliphatic and aromatic phosphines, and salts of organic or inorganic acids (e.g., salts of sulfinic acid). Specific examples include 4-(dimethylamino)phenylacetic acid, dimethylaminiophenethanol, dihydroxy p-toluidine, N-(3,5-dimethylphenyl)-N,N-diethanolamine, 2,4,6-pentamethylaniline, dimethylbenzylamine, N,N-dimethylacetamide, tetramethylurea, N-methyldiethanolamine, triethylamine, 2-(methylamino)ethanol, dibutylamine, diethanolamine, N-ethylmorpholine, trimethyl-1,3-propanediamine, 3-quinuclidinol, triphenylphosphine, sodium toluene sulfinate, tricyclohexylphosphine, N-methylpyrollidone, and t-butyldimethylaniline. These modifiers may be used alone or in combination with each other, or with a material having photoinduced potential greater than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone; an example of such a material is ethyl 4-(dimethylamino)benzoate ("EDMAB").

In other cases, it may be desirable to accelerate initiation of cationic polymerization. For example, in certain hybrid compositions it may be desirable to achieve near-simultaneous initiation of the free radically active functional groups and the cationically active functional groups. Examples of suitable initiation systems for accomplishing this objective are described in Oxman et al., entitled "Ternary Photoinitiator System for Curing of Epoxy/Polyol Resin Compositions" U.S. Pat. No. 6,025,406, and Oxman et al., entitled "Ternary Photoinitiator System for Curing of Epoxy Resins," U.S. Pat. No. 5,998,495, both of which are assigned to the same assignee as the present application and hereby incorporated by reference. As described therein, the photoinitiator system includes an iodonium salt (e.g., an aryliodonium salt), a visible light sensitizer (e.g., camphorquinone), and an electron donor. The systems have a photoinduced potential greater than or equal to that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone, measured according to the procedure described in the aforementioned Oxman et al. applications. An example of a suitable electron donor is ethyl 4-(dimethylamino)benzoate ("EDMAB").

In the case of hybrid compositions that include both free radically active functional groups and cationically active functional groups, it may be desirable to use one initiation system for free radical polymerization and a separate initiation system for cationic polymerization. The free radical polymerization initiation system is selected such that upon activation, only free radical polymerization is initiated.

One class of initiators capable of initiating polymerization of free radically active functional groups, but not cationically active functional groups, includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

A second class of initiators capable of initiating polymerization of free radically active functional groups, but not cationically active functional groups, includes free radical-generating photoinitiators, optionally combined with a photosensitizer or accelerator. Such initiators typically are capable of generating free radicals for addition polymerization at some wavelength between 200 and 800 nm. Examples include alpha-diketones, monoketals of alpha-diketones or ketoaldehydes, acyloins and their corresponding ethers, chromophore-substituted halomethyl-s-triazines, and chromophore-substituted halomethyl-oxadiazoles.

A third class of initiators capable of initiating polymerization of free radically active functional groups, but not cationically active functional groups, includes free radical-generating thermal initiators. Examples include peroxides and azo compounds such as AIBN.

The dual initiation systems further include a separate photoinitiation system for initiating polymerization of the cationically active functional groups. The cationic initiation system is selected such that activation of the free radical initiation system does not activate the cationic initiation system. Examples of suitable cationic photoinitiation systems for a dual initiation system composition include the onium salts and mixed ligand arene cyclopentadienyl metal salts with complex metal halide ions described above.

Polymerizable Components

The polymerizable compositions include cationically active functional groups and, optionally, free radically active functional groups. Materials having cationically active functional groups include cationically polymerizable epoxy resins. Such materials are organic compounds having an oxirane ring, i.e., a group of the formula

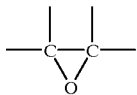

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

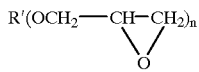

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-b is-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-metadioxane e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ gycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxctanes, spiro-orthocarbonates, spiro-orthoesters, and the like.

Materials having free radically active functional groups include monomers, oligomers, and polymers having one or more ethylenically unsaturated groups. Suitable materials contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaeiythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652, 274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these, free radically polymerizable materials can be used if desired.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

Other Additives

The polymerizable composition may further include a hydroxyl-containing material. Suitable hydroxyl-containing materials can be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000.

As used herein, all molecular weights are weight average molecular weights.

The hydroxyl-containing materials can be non-aromatic in nature or can contain aromatic functionality. The hydroxyl-containing material can optionally contain heteroatoms in the backbone of the molecule, such as nitrogen, oxygen, sulfur, and the like. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired polymerization conditions for the free radically active components of the polymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis (hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds; 2-butyne-1,4-diol; 4,4-bis (hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.) the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl-containing organic material used in the polymerizable compositions may vary over broad ranges, depending upon factors such as the compatibility of the hydroxyl-containing material with the epoxide and/or free radically polymerizable component, the equivalent weight and functionality of the hydroxyl-containing material, the physical properties desired in the final composition, the desired speed of polymerization, and the like.

Blends of various hydroxyl-containing materials may also be used. Examples of such blends include two or more molecular weight distributions of hydroxyl-containing compounds, such as low molecular weight (below 200), intermediate molecular weight (about 200 to 10,000) and higher molecular weight (above about 10,000). Alternatively, or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more monofunctional hydroxy materials with poly-functional hydroxy materials.

The polymerizable material(s) can also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, and tri-(meth) acrylate, sorbitol mono-, di-, tri-, tetra-, or penta-(meth) acrylate; and 2,2-bis[4-(2-hydroxy-3-methacryloxypropoxy)phenyl]propane.

The polymerizable material(s) can also contain hydroxyl groups and cationically active functional groups in a single molecule. An example is a single molecule that includes both hydroxyl groups and epoxy groups.

The polymerizable composition can also contain suitable additives such as fluoride sources, anti-microbial agents, accelerators, stabilizers, absorbers, pigments, dyes, viscosity modifiers, surface tension depressants and wetting aids, antioxidants, and other ingredients well-known to those skilled in the art. The amounts and types of each ingredient should be adjusted to provide the desired physical and handling properties before and after polymerization.

Polymerization Procedure

The polymerizable compositions are preferably prepared by admixing, under "safe light" conditions, the various components of the compositions. Suitable inert solvents may be employed if desired when effecting the mixture. Examples of suitable solvents include acetone, dichloromethane, and acetonitrile.

In the case of single initiation systems, polymerization is effected by exposing the composition to a radiation source, preferably a visible light source.

It is convenient to employ light sources that emit ultraviolet or visible light such as quartz halogen lamps, tungsten-halogen lamps, mercury arcs, carbon arcs, low-, medium-, and high-pressure mercury lamps, plasma arcs, light emitting diodes, and lasers.

In general, useful light sources have intensities in the range of 200–500 mW/cm$^2$. One example, which is particularly useful for dental applications, is a Visilux dental curing light commercially available from 3M Company of St. Paul, Minn. Such lights have an intensity of about 200 mW/cm$^2$ at a wavelength of 400–500 nm.

The exposure may be effected in several ways. For example, the polymerizable composition may be continuously exposed to radiation throughout the entire polymerization process. It is also possible to expose the composition to a single dose of radiation, and then remove the radiation source, thereby allowing polymerization to occur. In the case of hybrid compositions, the composition preferably is initially exposed to a single dose of radiation to initiate polymerization of the free radically active functional groups, followed by exposure to a second dose of radiation to initiate polymerization of the cationically active functional groups.

The invention will now be described further by way of the following examples.

EXAMPLES

Test Procedures

A. Hardness

The hardness of each composite following polymerization provides a measure of whether or not any particular filled composition inhibits or suppresses cationic polymerization. Two Barcol Hardness meters (models GYZJ-934-1 and GYZJ-935; Barber Coleman, Inc., Loves Park, Ill.) are used. These meters are monitored for performance consistency using a set of calibration disks provided with the meter.

Each prepolymerized composite is packed into a 5 mm diameter spherical cutout in a 4 mm deep Delrin mold. Mylar film is used as a liner on each side of the mold to ensure that the mold is filled completely, and that the sample is flush with the mold surface. The sample is then exposed to heat or actinic radiation to initiate polymerization.

Each sample is tested following polymerization using the two meters by pressing the tip of the tester firmly against the composite surface in a smooth, flat area of the sample. Two readings are taken at the top surface immediately after removing the heat or radiation source, and at 30 minutes, and the mean reading at each time point is reported. Both hardness meters are used in order to rank cure, with the the Barcol GYZJ-935 discriminating medium hard plastics, and the GYZJ-934-1 measuring hard plastics. All values registering less than 10 on GYZJ-934-1 are tested using GYZJ- 935. Samples registering above 80 on the GYZJ-935 meter are remade and retested on GYZJ-934-1 meter.

B. Isoelectric Point

The isoelectric point is measured using a Matec Electrokinetic Sonic Analysis System MBS-8000 (Matec Applied Sciences, Hopkinton, Mass.). The probe magnitude and polarity is calibrated with a 10% (v/v) Ludox solution. A 12 g sample of filler is dispersed into 228 g of distilled water to give an approximately 5% (w/w) dispersion. The zeta potential is measured while titrating over the pH range of 1 to 10 using 1.0 N HCl and 1.0 N NaOH. The zeta potential is plotted as a function of the pH. The isoelectric point is reported as the pH at which the zeta potential is equal to zero.

C. Adsorption Isotherm Analysis

Figure 5:
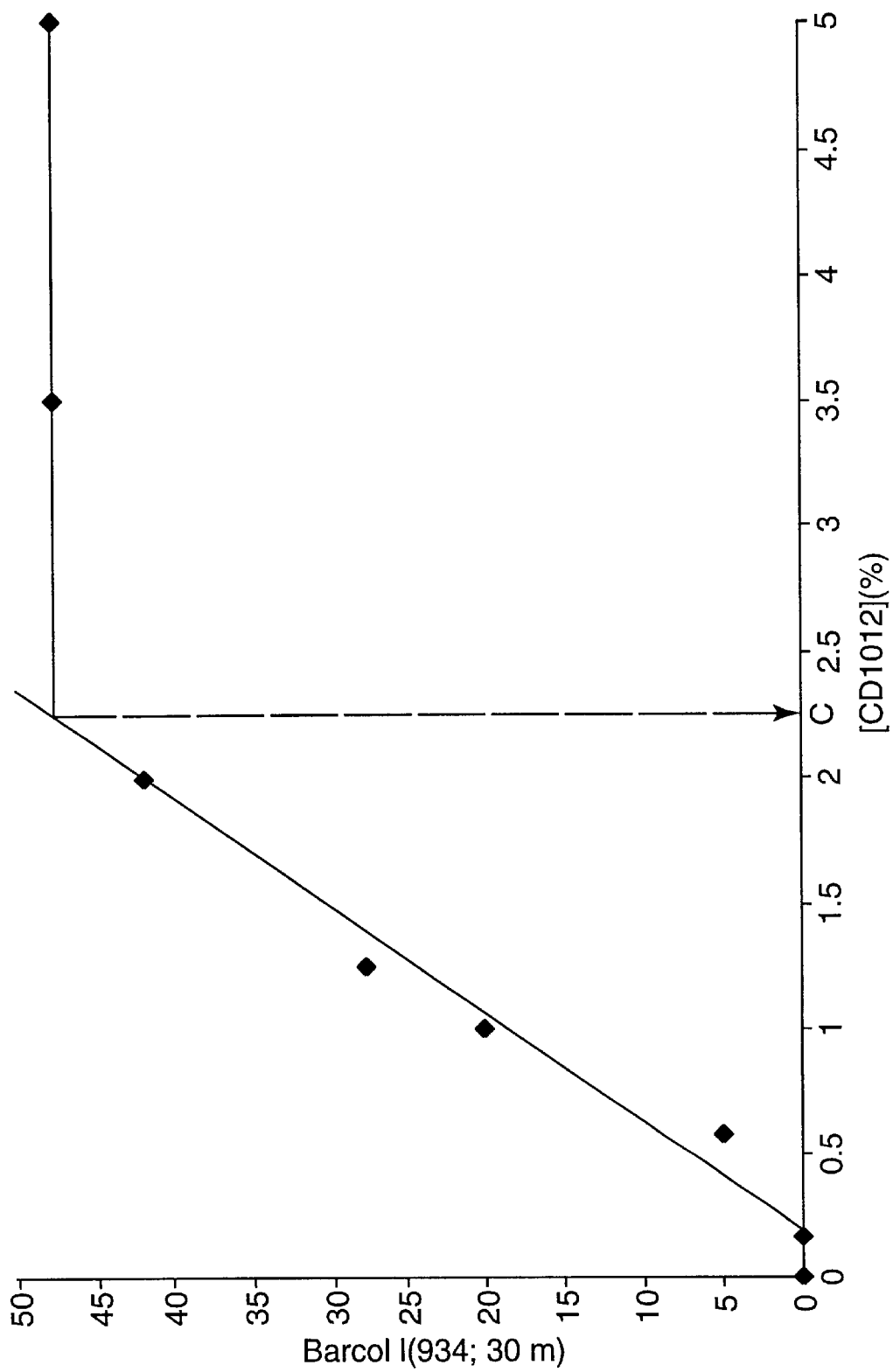
FIG. 5 is an adsorption isotherm analysis (Test Procedure C) featuring a plot of Barcol hardness (GYZJ-934-1) vs. photoinitiator concentration.

Fillers are dried at 150° C. for 1 week and stored in a desiccator. A surface area titration is performed by measuring the Barcol hardness (GYZJ-934-1 at 30 minutes post illumination) of a series of composites containing 70% (w/w) of a filler at photoinitiator concentrations ranging from 0.1% to 15% (w/w). In order to minimize refractive index mismatch with concomitant reduced depth of cure, resin B2 (described below) is chosen so that the refractive index of the resin blend approximately match that of the filler tested. The Barcol hardness (GYZJ-934-1 at 30 minutes) is plotted against the initial photoinitiator concentration in the resin (undiluted by filler), as shown in FIG. 5 in the case of a representative filler (filler (1), described below). The amount of photoinitiator-derived species adsorbed or inactivated on the surface of filler is calculated by determining the concentration of initiator required to achieve full cure (C). Since full cure in an unfilled resin systems is obtained at photoinitiator concentrations much lower that those used in this test of filled resins, the simplifying assumption is made that full cure is obtained even when vanishingly small concentrations of photoinitiator-derived species are present. This was confirmed by experiment.

The photoinitiator concentration can be expressed as $C=C_o-C_f$. When $C_f=0$, all initiator-derived species are adsorbed or inactivated, resulting in no cure of the resin. The maximum concentration of initiator-derived species adsorbed or otherwise inactivated by the filler is then given by $C=C_o$, as shown in FIG. 5.

The amount of the initiator-derived species that is adsorbed to the filler surface or otherwise inhibited is related to the adsorbance ($\Gamma$), BET surface area of the filler (SA) and the weight of the filler in the composite (W) as follows:

$$\text{Initiator adsorbed or inhibited}=(W)(SA)(\Gamma) \quad (1)$$

The amount of initiator in the resin (moles) is related to its concentration and the volume of the resin:

$$\text{Initiator change}=(V)(C) \quad (2)$$

V=volume of unfilled resin (mL)
C=concentration of initiator in resin
$C_o$=initial concentration of initiator in resin
$C_f$=final concentration of initiator in resin
W=weight of solids
SA=specific area of solids (m² /g) determined by BET
$\Gamma$=adsorbance of initiator derived species normalized to filler surface area($\mu$moles/m²)
$\Gamma'$=adsorbance of initiator derived species ($\mu$moles/g filler)

The adsorbance of the photoinitiator-derived species ($\Gamma'$; $\mu$moles/g filler) or the adsorbance per unit surface area of filler ($\Gamma$; $\mu$moles/m²) is calculated. In order to solve for the adsorbance, we note that within the parameters of the material set, the presence of even vanishingly small amounts of photoinitiator will cause complete cure in the absence of filler in the time frame of the test. For example, in the absence of filler, complete cure is obtained at concentrations of less than 0.1% (w/w) iodonium (CD1012) whereas most screening tests utilize 1–15% (w/w) iodonium. Therefore, for these tests, we can assume that the presence of any uninhibited photoinitiator derived species would result in substantial cure in the presence of filler at 30 minutes. Therefore, we can relate the inhibition of cure, as measured by Barcol hardness, to the concentration of photoinitiator-derived species that are adsorbed or deactivated by equating equations (1) and (2):

$$\text{initiator change}=\text{initiator derived species adsorbed or deactivated} \quad (3a)$$

$$(V)(C_o)=(W)(SA)(\delta) \quad (3b)$$

Rearranging, we can solve for the adsorbance ($\Gamma$) in equation (4)

$$\Gamma=(V)(C_o)/(W)(SA) \quad (4)$$

The dependence on the BET surface area can be removed from the adsorbance by multiplying, as in equation (5), to give the absorbance per gram of filler.

$$\Gamma'=\Gamma \times SA \quad (5)$$

D. Conductivity

Fillers are dried at 150° C. for 1 week and stored in a desiccator. Methyl ethyl ketone and anhydrous ethanol supplied by J. T. Baker (Phillipsburg, N.J.) are dried over molecular sieves. Exposure to humid, ambient conditions is avoided. A stock solution is prepared containing 0.25 parts CPQ, 1.5 parts Sartomer CD1012, 0.5 parts ethyl-4-dimethylaminobenzoate and 97.75 parts of a 90/10 weight/weight methyl ethyl ketone/anhydrous ethanol solution. A sample of 4 grams of stock solution is weighed into a glass vial. A calibrated glass pH electrode (Corning PN 476540) is placed into the solution and a Beckman 210 pH meter is zeroed on the solution. The pH meter is standardized periodically in pH4 and pH7 buffer solutions.

The vial is irradiated for 20 seconds with a 3M™ XL 3000™ dental curing light. The initial solution conductivity is read in millivolts and recorded as $E_0$. 1.0 g sample of filler is added to the 4 g of irradiated stock solution and stirred vigorously for up to 45 seconds. The conductivity is measured and allowed to come to equilibrium. The final conductivity is measured and recorded as E. The conductivity change is expressed as the difference between the initial and final conductivity.

After obtaining the final conductivity reading, the electrode is rinsed with a dried mixture of 2-butanone and ethanol, gently wiped, and allowed to dry for 30–60 seconds prior to use on the next test.

E. FTIR Analysis

Fillers are dried at 150° C. for 1 week and stored in a desiccator. Samples are prepared as Nujol mulls. Four drops (approximately 0.08 ml) of ethyl acetate (Fluka Chemika 99.5% (GC)) are added to a 1 cc portion of Nujol (mineral oil USP—Paddock Laboratories, Inc.). Approximately two drops (approximately 0.04 ml) of the Nujol/ethyl acetate mixture is added to approximately 300 mg of dried filler (150° C. for 1 week) and mulled to form a highly filled, cohesive mull. The sample is placed between NaCl plates for presentation to the FTIR. The NaCl plate is sanded on one surface with 500 grit Wet-or-Dry sandpaper (3M Company) to present a rough surface to facilitate spreading the mull and to prevent interference fringes seen when polished surfaces are used.

All spectra are recorded in the absorbance mode on the Bomem MB-102 FTIR (Bomem/Hartman & Braun, Quebec, Quebec Canada). Sixteen scans (at 4 cm$^{-1}$ resolution) are co-added per spectrum. In the absence of filler, ethyl acetate in Nujol shows an absorbance band at 1747 cm$^{-1}$. The relative ratio of peak height at 1747 cm$^{-1}$ to that of the total peak height due to ethyl acetate in the presence of filler is calculated. For example, when the presence of filler causes a shift to 1703, 1710 and 1726 cm$^{-1}$, the relative peak height is calculated as follows:

$$\% P_{H,1747\ cm-1} = (100 * P_{H,1747}) / [P_{H,1747} + P_{H,1703} + P_{H,1710} + P^{H,1726}].$$

A value % $P_{H,1747\ cm-1}$ of 100% denotes no interaction of the filler surface with ethyl acetate.

The measurement of peak height was done using a commercial program (Grams32 Galactic) which allows the use of preselected baseline points (from a "flat" area of the spectrum) and the selection of the height to be measured.

F. Depth of Cure

Three composite pastes are prepared by combining 3 parts of resin with 7 parts of filler. The pastes are filled into syringes, and de-bubbled under pressure at 45° C. for 24 hours. The pastes are then extruded into cylindrical nylon molds (diameter≅6 mm) with heights ranging from 2 to 8 mm. The filled molds are warmed to 37° C. by placing them in an oven for 30 minutes, after which time they are irradiated for 60 seconds with a 3M model 5530 dental curing light. The irradiated samples are then returned to the 37° C. oven. Thirty minutes later the samples are removed and tested for Barcol hardness (GYZJ-934-1) on the bottom of the sample, as described in Test Procedure A.

G. Karl Fisher Titration

The moisture content of fillers is measured using a 652KF Coulometer (Metrohm, Houston, Tex.). Samples are prepared in a dry box. Approximately 1 g of filler is weighed into a serum vial. A 10 mL sample of methanol is added to the vial which is sealed with a serum cap and weighed. Samples are placed a shaker for 2–6 hours, after which time the filler is allowed to settle by standing overnight. Three vials are prepared per filler sample for triplicate readings.

A sample of the supernatant is withdrawn from the vial using a 20 gauge needle and syringe. A 0.45 micron filter is then placed on the end of a syringe and the filtered sample injected into the Karl Fischer titrator. The sample is titrated iodometrically as described in *Quantitative Chemical Analysis* (Harris).

H. B.E.T. Surface Area

The surface area is determined using nitrogen adsorption in a single-point Brinauer-Emmet-Tell (BET) method, as described by S. J. Gregg and K. S. W. Sing in *Adsorption, Surface Area, and Porosity* (Academic Press Inc., London 1982). Approximately 12 grams of sample is placed into the chamber of the Horiba SA-6210 (Irvine, Calif.) sample preparation station and degassed for 10–12 hours at 200 C. The surface area of the sample is measured on a Horiba SA-6201 twice, and both the outgassed and repeated measurement are compared. The out gassed measurement is reported.

I. Particle Size

Particle size is measured using a Horiba LA-910 laser light scattering instrument. Particle size is measured in three media. The particle size of dry filler is measured using the Horiba dry powder attachment, Powderjet. The primary particle size of filler when dispersed in aqueous solution is measured by dispersing 0.2–0.4% (w/w) filler into a buffered aqueous solution containing Liquinox, Tween 80, Calgon, and NaF and applying an ultrasonic horn and a magnetic stirrer for 10 minutes. Sufficient sample is added to a solution of surfactant solution in the test chamber in order to give a transmittance of approximately 85%. Particle size is reported as the mean volume diameter (microns).

J. Refractive Index ($n_D$)

The refractive index of the filler particles is measured using the Becke Line Method, as described in *Practical Refractometry by Means of a Microscope* (Roy M. Allen, 2$^{nd}$ Edition, Cargille, N.J.).

K. Specific Gravity

Specific gravity (g/cc) is measured using a Micromeritics (Norcross, Ga.) AccuPyc 1330 helium pycnometer.

L. X-Ray Diffraction (XRD)

X-ray diffraction is performed with copper K-alpha radiation on either a Phillips vertical diffractometer or a Picker 4 circle diffractometer. "Am" means amorphous, "unid.ph." means unidentified phase, "unid.crys.ph." means unidentified crystalline phase, "T" means tetragonal structure, "pc" means pseudo-cubic structure, "c" means cubic structure, and "crist. unid." means alpha-cristobalite and unidentified crystalline phase.

M. Fluorescence

Fluorescent behavior of fillers is observed under illumination by a Spectroline ENF-260C long wavelength UV light (Spectronics Corp., Westbury, N.Y.). Bright fluorescence is noted with a capital letter of the color observed; dull fluorescence is noted with a small letter (y=yellow, w=white, b=blue). No fluorescence is noted with the letter "N".

N. Radiopacity

The radiopacity of polymerized samples is determined according to the procedure specified in Section 7.11 of the International Standard ISO 4049:1988 (E).

O. Diametrile Tensile Strength (DTS)

For DTS measurements the uncured composite samples were injected into 3.2 mm inner diameter, 9.5 mm outer diameter rigid acrylic tubes. The filled tubes were subjected to 2.2–2.9 kg/cm$^2$ (30–40 psi) pressure for 5 minutes, followed by curing while under pressure by exposure to two Visilux-2 (3M, St. Paul) dental curing lights for 80 seconds. The cured samples were allowed to stand for 5 minutes without applied pressure and then were placed in 37° C. deionized water for 1–2 hours before cutting to length. The samples were cut on a diamond saw to form cylindrical plugs approximately 1.5 mm long for measurement of diametrile tensile strength. Five samples of each material were prepared for DTS results. The plugs were stored in deionized water at approximately 37° C. for about 16–24 hours and their DTS values then determined according to American Dental Association specification No. 27 using an Instron Mechanical Testing Instrument (Model 1123).

P. Compressive Strength (CS)

For CS measurements the uncured composite samples were injected into 3.2 mm inner diameter, 9.5 mm outer diameter rigid acrylic tubes. The filled tubes were subjected to 2.2–2.9 kg/cm$^2$ (30–40 psi) pressure for 5 minutes, followed by curing while under pressure by exposure to two Visilux-2 (3M, St. Paul) dental curing lights for 80 seconds. The cured samples were allowed to stand for 5 minutes without applied pressure and then were placed in 37° C. deionized water for 1–2 hours before cutting to length. The samples were cut on a diamond saw to form cylindrical plugs approximately 6 mm long for measurement of compressive strength. Five samples of each material were prepared for CS results. The plugs were stored in deionized water at approximately 37° C. for about 16–24 hours and their CS values then determined according to American Dental Association specification No. 27 using an Instron Mechanical Testing Instrument (Model 1123).

Q. Visual Opacity

Disc-shaped, one millimeter thick by 20 millimeter diameter samples of the composite were cured by exposing them to illumination from a 3M Visilux-2 dental curing light for 60 seconds on each side of the disk at a distance of 6 millimeters. The cured composite samples were then evaluated for visual opacity by measuring transmission of light through the thickness of the disk using a MacBeth transmission densitometer Model TD-504 equipped with a visible light filter.

Composite Preparation

Six different polymerizable resin compositions were made by preparing a series of stock solutions and then combining a given stock solution with a given initiator solution. The various stock solutions are described below. All amounts are given in w/w percent. The stock solutions were prepared by mixing the components using a Vertishear Cyclone I.Q. at 600 rpm for 10 minutes on ice.

STOCK SOLUTIONS

| Component | Stock A1 | Stock A2 | Stock A3 | Stock A4 |
|---|---|---|---|---|
| pTHF | 20 | 20 | 20 | 15.5 |
| UVR6105 | 80 | 20 | 40 | 42.2 |
| Epon 828 | 0 | 40 | 40 | 0 |
| GY281 | 0 | 0 | 0 | 42.2 | pTHF is polytetrahydrofuran 250 (M.W. 250) available from Aldrich Chemical Co. (Milwaukee, Wis.).

UVR 6105 is an epoxy resin available from Union Carbide Co. (Danbury, Conn.).

Epon 828 is an epoxy resin available from Shell Chemical Co. (Houston, Tex.).

GY281 is a bisphenol F epoxy resin from Ciba Geigy.

An initiator solution was combined with one of the stock solutions to form a polymerizable resin solution by mixing the two solutions using a Vertishear Cyclone I.Q. at 15,000 rpm for 40 minutes on ice for polymerizable resin solutions are shown below. All amounts are given in w/w percent.

Polymerizable Resin Compositions

| Component | Resin B1 | Resin B2 | Resin B3 | Resin B4 | Resin B5 |
|---|---|---|---|---|---|
| CD1012 | 1.25 | 1.25 | 1.25 | 1.25 | 20 |
| CPQ | 0.5 | 0.5 | 0.5 | 0.5 | 8 |
| EDMAB | 0 | 0 | 0.1 | 0.1 | 0 |
| Stock A | 98.25(A1) | 98.25(A2) | 98.15(A3) | 98.15(A4) | 72(A5) |

CD1012 is diaryliodonium hexafluoroantimonate available from Sartomer (Exton, Pa.).

CPQ is camphorquinone available from Aldrich Chemical Co.

EDMAB is ethyl-4-dimethyl available from Aldrich Chemical Co.

Resin B6 is a vinyl ether-based composition prepared by mixing 0.5% (w/w) CPQ, 1.5% (w/w) CD1012, and 90% (w/w) Vectomer 4010 vinyl ether resin to form a stock solution, and then combining 99.5% (w/w) of the stock solution with 0.5% (w/w) para-dimethylamino benzoic acid.

Two gram composite samples for testing were prepared by hand spatulation. Polymerizable resin composition B was weighed into a white plastic container and an appropriate amount of filler added using a Mettler balance AE200 (Mettler Instrument Corp., Highstown, N.J.). The sample was then mixed using a plastic stir rod until the filler was well-dispersed in the resin (approximately 1–5 minutes). All effort was made to shield the sample from room light. All preparation and analysis was performed under yellow lights to prevent photoinitiated reaction.

Composite samples were polymerized using visible, UV light, and/or heat. Visible light polymerization was done using a 3M Visilux 2™ which is a filtered lamp that emits light in the range of wavelengths of approximately 400 nm to 480 nm. Each sample was irradiated by placing the lamp flush against the composite surface (covered in Mylar), placed on a mirror, for 120 seconds (60 seconds top and bottom).

In some examples, the sample was cured using UV light. In these cases, Sylvania 350 Black light bulbs F15T8/350BL (15 watt) and Fusion H and D light sources (Fusion Systems, Rockville, Md.) were used. The light output (mJ/cm$^2$) was measured using a Dynachem 500 UV Integrated Radiometer (Tustin, Calif.).

EXAMPLES 1–4

These examples demonstrate the use of various screening tests to select radiopacifying filler/resin/initiator combinations that, upon polymerization, form a polymerized composition having a Barol hardness, measured according to Test Procedure A using the GYZJ-935 meter, of at least 10 within 30 minutes following initiation of the cationically active functional group at a reaction temperature of 25° C. The screening tests were developed by examining the interaction of both radiopacifying and radiolucent fillers with various cationically polymerizable compositions. The fillers used in these examples were prepared as follows:

Filler (a)

Filler sample (a) was prepared by heating Raysorb™ T3000 glass (ESS-Tech, Essington, Pa.) in a furnace at 600° C. for 18 hours. Raysorb™ T3000 is a barium aluminoborosilicate glass which according to the vendor, contains 33% barium oxide.

Filler (b)

Filler sample (b) was Raysorb™ T3000 as received from the manufacturer.

Filler (c)–(e)

Filler samples (c)–(e) were prepared by a conventional melt process. Lanthanum oxide, silicon oxide, aluminum oxide, boric acid, and sodium carbonate were weighed out to yield the oxide compositions shown in Table 1. The batch ingredients were blended, charged to a platinum crucible, heated to 1400–1500° C. for a sufficient time to assure a homogeneous melt, quenched in water, and dried. The glass for samples (c) and (d) was crushed in an alumina plate grinder to yield frit less than approximately 2 mm diameter. The glasses for samples (c), (d), and (e) were milled in a porcelain jar mill with 0.5" alumina media; 1 part by weight of ethanol per 99 parts glass was charged to the mill. The milling time for sample (c) was 24 hr; for sample (d), 48 hr; for sample (e), 24 hr.

Filler (f)

Filler sample (f) was prepared as follows. 25.5 parts silica sol ("Ludox" LS: E.I. duPont de Nemours & Co.) were acidified by the rapid addition of 0.255 parts concentrated nitric acid. In a separate vessel, 12.9 parts ion-exchanged zirconyl acetate (Magnesium Elektron, Inc.) were diluted with parts deionized water and the resultant solution acidified with 0.255 parts concentrated nitric acid. The silica sol was pumped into the stirred zirconyl acetate solution and mixed for one hour. The stirred mixture was filtered through a 3 micrometer filter followed by a 1 micrometer filter. The filtrate was poured into trays to a depth of about 25 mm and dried at 65° C. in a forced air oven for about 35 h. The resultant dried material was removed from the oven and tumbled through a rotary tube furnace (Harper Furnace Corp.) preheated to 950° C. The calcined material was comminuted in a tumbling ball mill with ¼" alumina media until an average particle size of 0.5–1.2 micrometers (as measured on a Micromeritics 5100 sedigraph) is obtained; the mill charge included 75 parts calcined material, 3 parts methanol, 1.9 parts benzoic acid, and 1.1 parts deionized water. The filler was then loaded into ceramic saggers and fired in an electric furnace (L&L Furnace Corp.) in air at 880–900° C. for approximately 8 hr. The fired filler was then ball-milled for 4–5 hr; the mill charge included 32 parts fired filler, 1.25 parts ethanol, and 0.3 parts deionized water. Next the filler was passed through a 74 micrometer nylon screen in a vibratory screener (Vortisiv V/S 10010); the filler was then blended in a V-blender (Patterson-Kelly Corp.) for about 15 min.

Filler (g)

Filler sample (g) was prepared as follows. Calcined material prepared as in sample (f) was comminuted in a tumbling ball mill with ¼" alumina media until an average particle size of 1.1–1.8 micrometers (as measured on a Micromeritics 5100 sedigraph) is obtained; the mill charge included 94.4 parts calcined material, 1.4 parts methanol, and 4.1 parts deionized water. The filler was then loaded into ceramic saggers and fired in an electric furnace (Harper Furnace Corp.) in air at 800–1000° C. for approximately 9 hr. The fired filler was then ball-milled for 4–5 hr; the mill charge included 34 parts fired filler, 3.4 parts methanol, and 0.85 parts deionized water. Next the filler was passed through a 74 micrometer nylon screen in a vibratory screener (Vortisiv V/S 10010); the filler was then blended in a V-blender (Patterson-Kelly Corp.) for about 15 min.

Filler (h)

Filler sample (h) was prepared in the same way as filler sample (f), except that the firing condition was 1000° C. for 4 hr instead of 880–900° C. for approximately 8 h. After firing, the filler was ball milled with alumina media for 72 h; the charge included 900 parts filler, 20 parts ethanol, and 5 parts deionized water. The mill was opened at 24 h and 48 h, and any packed filler was dislodged.

Filler (i)

Filler sample (i) was prepared as follows. 1.42 parts by weight of boric acid (33906-7: Aldrich Chemical Company, Inc., Milwaukee) were added to 19.87 parts of colloidal silica sol (1042: Nalco Chemical Company, Naperville) under vigorous stirring. After addition of 15.32 parts deionized water, stirring was continued until the boric acid was fully dissolved. In another vessel 31.83 parts of zirconyl acetate (Magnesium Elektron, Inc.) was charged; under vigorous stirring 1.34 parts ACS grade nitric acid was added to the zirconyl acetate. The colloidal silica preparation was added to the zirconyl acetate preparation under vigorous stirring; stirring was continued for 1 hr. The sol was spray dried in a 3-ft. Niro spray drying unit with a rotary atomizer set at 20,000 RPM; the resulting powder was fine and free-flowing. The spray dried powder was loaded into ceramic saggers and calcined in air in an electric furnace (Cress Mfg. Company, El Monte, Calif.) according to the profile: ramp to 200° C., soak for 1 hr, ramp to 550° C., hold for 4 hr, cool to room temperature. The powder was then ball-milled with ¼" alumina media for 32 hr; the charge included 260 parts by weight powder, 6.5 parts benzoic acid, 10.4 parts methanol, and 4 parts deionized water. The resulting powder was then loaded into ceramic saggers and fired in air in an electric furnace (ramp to 900° C. at 14° C./min, hold for 12 hr, cool to room temperature). The powder was then ball-milled for 24 hr with ¼" alumina media; the charge included 400 parts by weight of powder, 4 parts of ethanol, and 1 part of deionized water.

Filler (j)

Filler sample (j) was prepared in the same manner as (i) except that the firing temperature was 750° C. instead of 900° C.

Filler (k)

Filler sample (k) was prepared in the same manner as (i) except that the firing temperature was 850° C. instead of 900° C.

Filler (l)

Filler sample (l) was prepared as follows. A portion of filler sample (m) was loaded into ceramic saggers and fired in air in an electric furnace (Cress Mfg. Company, El Monte, Calif.) according to the profile: ramp to 1000° C., hold for 4 hr, cool to room temperature. The filler was then ball-milled for 24 hr with ¼" alumina media; the charge included 1145 parts by weight of filler, 40 parts of ethanol, and 10 part of deionized water.

Filler (m)

Filler sample (m) was prepared as follows. 19.297 parts by weight of aluminum formoacetate ("AFA") were charged to a vessel. The AFA was prepared as follows. A flask was charged with 400 g of deionized water, 34.5 ml of glacial acetic acid, and 25.6 ml of concentrated formic acid. The resulting solution was brought to a roiling boil, after which 26.98 g of aluminum metal powder were added in three portions of roughly 9 g each over a 2 hour period. An exothermic reaction ensued after the initial addition, and the rate of the reaction was moderated by the addition of room temperature deionized water. The digestion was continued for 10 h, after which the solution was cooled and filtered to yield 9.25 wt. % of $Al_2O_3$ (pH=4.45).

In a separate vessel a solution of 1 part by weight of lanthanum nitrate hexahydrate to 1 part deionized water was prepared. Under vigorous stirring, 16.347 parts of the lanthanum nitrate hexahydrate solution was added to the aluminum formoacetate preparation and stirred for 1 hr. 7.647 parts of colloidal silica sol sol (1042: Nalco Chemical Company, Naperville) was added to the preparation under vigorous stirring, and stirred for 1 hr. 1.208 parts of ACS grade nitric acid was added to the preparation under vigorous stirring, and stirred for 20 min. The sol was spray dried in a 3-ft. Niro spray drying unit with a rotary atomizer set at 20,000 RPM; the resulting powder was fine and free-flowing. The spray dried powder was loaded into ceramic saggers and calcined in air in an electric furnace (Cress Mfg. Company, El Monte, Calif.) according to the profile: ramp to 200° C., soak for 1 hr, ramp to 550° C., hold for 4 hr, cool to room temperature. The powder was then ball-milled with ¼" alumina media for 6 hr; the charge included 900 parts by weight powder and 4 parts deionized water.

Filler (n)

Filler sample (n) was prepared as follows. Quartz rock was heated to about 660° C., quenched in water, drained, then dried in a forced air oven for 16 hours at about 200° F. The quenched quartz was combined with quartz media into a mill and tumbled for about 70 hours; the charge included 99 parts by weight quenched quartz and 1 part methanol. The resulting particles were blended with 0.1 wt. % carbon black in a V-blender for 1 hour, then fired in an electric furnace at about 950° C. for 4 hours. The resulting particles were passed through a 100 micrometer nylon screen, then blended in a V-blender for 30 minutes.

Filler (o)

Filler sample (o) was prepared as follows. Fused quartz tubing of 1 mm wall thickness was broken into shards with a hammer before ball-milling with 0.5 inch alumina media for 24 hour; the charge contained 99 parts by weight of the shards and 1 part ethanol.

Filler (p)

Filler (p) was a commercially available calcium carbonate filler (Huber) Quincy, Ill.

Filler (q)

Filler (q) was a commercially available calcium carbonate filler (ECC International, Sylacauga, Ala.).

Filler (r)

Filler (r) was a commercially available feldspar filler (The Feldspar Corp., Atlanta, Ga).

Filler (s)

Filler (s) was $KBF_4$ obtained from Atotech of Rock Hill, S.C.

Filler (t)

Filler (t) was a melt-derived cryolite filler obtained from Tarconord A/A, Avernakke, Denmark.

Filler (u)

Filler (u) was a synthetic cryolite obtained from Kali-Chemie Corp., Greenwich, Conn.

Filler (v)

Filler (v) was a treated titanium dioxide obtained from DuPont (Wilmington, Del.) (IT-Pure Series).

Filler (w)

Filler (w) was a blend of 30% (w/w) filler (f) and 40% (w/w) filler (n).

Filler (x)

Filler (x) was a blend of 9% (w/w) ytterbium trifluoride (Aldrich Chemical Co.) and 61% (w/w) filler (n).

The chemical compositions of fillers (a)–(m) are summarized below in Table 1. All amounts are given in weight percent. In the case of fillers (a) and (b), the amount of BaO is based upon information reported by the vendor.

TABLE 1

| Filler | Al2O3 | B2O3 | BaO | La2O3 | SiO2 | ZrO2 | Other |
|---|---|---|---|---|---|---|---|
| (a) | | | 33 | | | | |
| (b) | | | 33 | | | | |
| (c) | 20 | 20 | | 30 | 30 | | |
| (d) | 20 | 20 | | 30 | 30 | | |
| (e) | 20 | 20 | | 20 | 30 | | 10Na2O |
| (f) | | | | | 72.8 | 27.2 | |
| (g) | | | | | 72.8 | 27.2 | |
| (h) | | | | | 72.8 | 27.2 | |
| (i) | | 5.4 | | | 45.9 | 48.7 | |
| (j) | | 5.4 | | | 45.9 | 48.7 | |
| (k) | | 5.4 | | | 45.9 | 48.7 | |
| (l) | 35.7 | | | 12.3 | 52 | | |
| (m) | 35.7 | | | 12.3 | 52 | | |

Fillers (a)–(v) were characterized according to Test Procedures G–M. The results are summarized below in Table 2. The designation"—means not tested.

In the case of the particle size data, the figure in parentheses represents the standard deviation. The letters B, M, and T reflect the particle size distribution and correspond to Mono-modal, Biomodal, and Trimodal, respectively.

TABLE 2

| Filler | $n_D$ | XRD | Fluorescence | BET ($m^2/g$) | Particle size ($\mu m$) | Sp. Gravity (g/cc) | Karl Fisher (%) |
|---|---|---|---|---|---|---|---|
| (a) | 1.546 | — | N | 1.45 | 2.132 (3.221)B | 3.0147 | 0.02 |
| (b) | 1.553 | — | N | 1.60 | 3.731 (5.604)B | 2.9744 | 0.0037 |
| (c) | 1.585 | — | N | 3.35 | 5.402 (4.680)B | 2.9984 | 0.04 |
| (d) | 1.585 | — | N | 3.57 | 1.906 (2.570)T | 3.0774 | 0.066 |
| (e) | — | — | N | 1.90 | 13.18 | 2.7732 | 0.15 |
| (f) | 1.542 | — | N | 54.55 | 2.347 (3.714)B | 2.6877 | 0.24 |
| (g) | 1.542 | — | N | 10.65 | 1.019 (1.072) | 2.7080 | 0.12 |
| (h) | — | — | — | 68.93 | 0.799 (0.608)M | 2.6902 | 0.28 0.80 |
| (i) | 1.542 | — | — | 14.99 | 0.837 | 3.273 | 0.25 |
| (j) | — | — | — | 51.14 | 1.179 ((2.109)B | 3.0477 | 0.66 |
| (k) | — | — | — | 13.51 | 0.649 (0.358)M | 3.1395 | 0.35 |
| (l) | 1.533 | — | — | 32.47 | 4.019 (4.838)B | 2.639 | 0.25 |

TABLE 2-continued

| Filler | $n_D$ | XRD | Fluor-escence | BET ($m^2/g$) | Particle size ($\mu m$) | Sp. Gravity (g/cc) | Karl Fisher (%) |
|---|---|---|---|---|---|---|---|
| (m) | 1.528 | AM | W/B | 165.74 | 11.830 (7.644)B | 2.5094 | 3.46 |
| (n) | 1.544 | — | — | 6.70 | 3.328 (5.219)B | 2.6267 | 0.078 |
| (o) | 1.459 | — | — | 2.92 | 1.017 (0.789)B | 2.2871 | 0.042 |
| (p) | 1.57 | — | — | 1.04 | 16.55 | 2.737 | 0.08 |
| (q) | 1.57 | — | — | 3.03 | 5.66 | 2.740 | 0.05 |
| (r) | 1.537 | — | — | 1.07 | 20.19 | 2.635 | 0.04 |
| (s) | 1.325 | — | — | 0.48 | 20.70 | 2.517 | 0.03 |
| (t) | 1.34 | — | — | 1.03 | 17.69 | 3.00 | 0.04 |
| (u) | 1.34 | — | — | 0.46 | 13.71 | 2.875 | 0.02 |
| (v) | — | — | — | — | 0.781 (0.297)M | — | — |

EXAMPLE 1

This example demonstrates that the isoelectric point may be used as a screening test. Isoelectric points for various filler compositions were determined according to Test Procedure B. Samples for hardness testing were prepared at 50% (w/w) and 70% (w/w) filler loading according to the general procedure described above. The resin in each case was Resin B2. Samples were cured with visible light using a 3M Visilux 2™ light. The sample was irradiated by placing the lamp flush against the composite surface (covered with Mylar) for 120 seconds (60 seconds on both top and bottom). The composite was placed against a mirror during curing.

Hardness was evaluated according to Test Procedure A. The results are summarized in tabular form in Tables 3A and 3B. "No cure" meant that the composite did not register on either of the two hardness meters, i.e., when the Mylar film was removed from the mold, the uncured resin pulled away with the film or was easily penetrated. The results using the GYZJ-935 meter are also shown graphically in FIGS. 1(a) (50% (w/w) filler loading) and 1(b) (70% (w/w) filler loading). A Barcol value of −5 denotes no cure.

These results demonstrate that, in general, for filler loadings of 50% (w/w) or greater, radiopacifying fillers having isoelectric points no greater than 7 can be used successfully.

There were some fillers (fillers (f), (h), (v) at 50% loading and fillers (b), (f), (h), and (v) at 70% loading) which did not successfully polymerize even though they had IEP values no greater than 7. However, these fillers did satisfy other screening tests, as described below. These results demonstrate that the individual screening tests preferably should be used in combination with each, other for the best results.

TABLE 3A

| Filler | IEP | 50% (w/w) Filler GYZJ-934-1 | GYZJ-935 |
|---|---|---|---|
| (a) | 2.8 | 18 | 82 |
| (b) | 3.1 | 22 | 88 |
| (c) | 6.4 | 22 | 88 |
| (d) | 6.5 | 28 | 82 |
| (e) | NA | No Cure | No Cure |
| (f) | 2.2 | No Cure | No Cure |
| (g) | 2.4 | 22 | 82 |
| (h) | 3.6 | No Cure | No Cure |

TABLE 3A-continued

| Filler | IEP | 50% (w/w) Filler GYZJ-934-1 | GYZJ-935 |
|---|---|---|---|
| (i) | 2.2 | 8 | 82 |
| (j) | 3.9 | 18 | 88 |
| (k) | 4.1 | 18 | 82 |
| (l) | 5.5 | 22 | 88 |
| (m) | 7.6 | No Cure | No Cure |
| (n) | 1.2 | 42 | 98 |
| (o) | 2.5 | 32 | 92 |
| (p) | 9.5 | No Cure | No Cure |
| (q) | 9.5 | No Cure | No Cure |
| (r) | 2 | 32 | 92 |
| (s) | — | 22 | 82 |
| (t) | 4.5 | 22 | 88 |
| (u) | 5.5 | 22 | 88 |
| (v) | 6.9 | — | — |

TABLE 3B

| Filler | IEP | 70% (w/w) Filler GYZJ-934-1 | GYZJ-935 |
|---|---|---|---|
| (a) | 2.8 | 25 | 95 |
| (b) | 3.1 | No Cure | No Cure |
| (c) | 6.4 | 50 | 95 |
| (d) | 6.5 | 25 | 95 |
| (e) | NA | No Cure | No Cure |
| (f) | 2.2 | No Cure | No Cure |
| (g) | 2.4 | 0 | 0 |
| (h) | 3.6 | No Cure | No Cure |
| (i) | 2.2 | 30 | 95 |
| (j) | 3.9 | 0 | 95 |
| (k) | 4.1 | 5 | 90 |
| (l) | 5.5 | 35 | 95 |
| (m) | 7.6 | No Cure | No Cure |
| (n) | 1.2 | 50 | 95 |
| (o) | 2.5 | 40 | 100 |
| (p) | 9.5 | No Cure | No Cure |
| (q) | 9.5 | No Cure | No Cure |
| (r) | 2 | 0 | 85 |
| (s) | — | 20 | 90 |
| (t) | 4.5 | 0 | 90 |
| (u) | 5.5 | 30 | 85 |
| (v) | 6.9 | — | No Cure |

EXAMPLE 2

This example demonstrates that adsorption isotherm analysis may be used as a screening test. Adsorption values for various filler compositions were determined according to Test Procedure C. Samples for hardness testing were prepared at 50% (w/w) and 70% (w/w) filler loading as in Example 1. The resin in each case was Resin B2.

The absorption value (Γ) is reported in μmoles/g filler as the observed adsorption multiplied by the B.E.T. surface area of the filler (see Table 2).

Figure 2B:
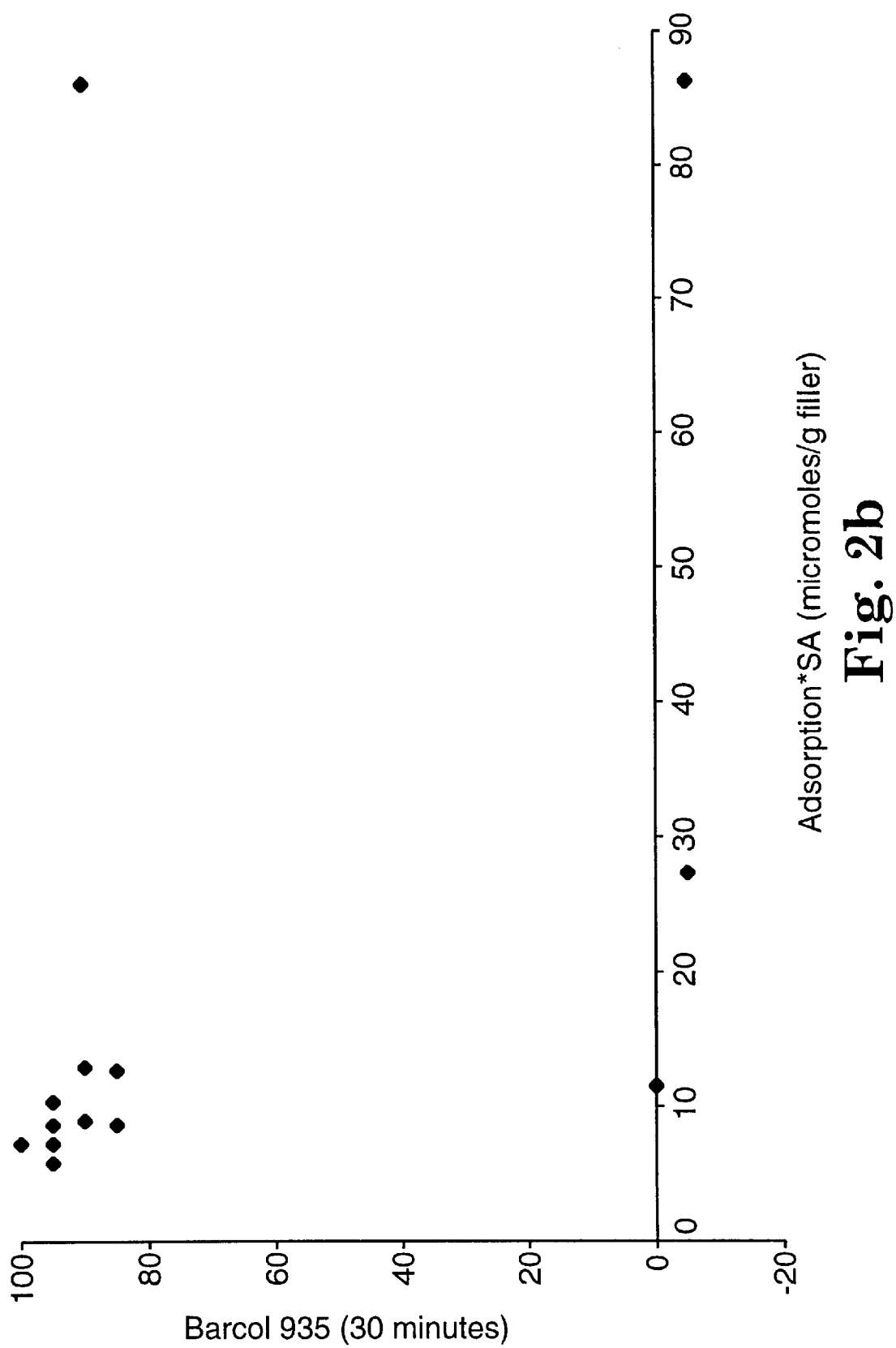

Hardness was evaluated as in Example 1. The results are summarized in tabular form in Tables 4A and 4B. The results using the GYZJ-935 meter are also shown graphically in FIGS. 2(a) (50% (w/w) loading) and 2(b) (70% (w/w) loading). A Barcol value of −5 denotes no cure.

These results demonstrate that, in general, for filler loadings of 70% (w/w), filler compositions exhibiting adsorption values of no greater than about 20 micromoles/g filler, measured as described above, can be used successfully. For filler loadings between 50 and 70% (w/w), filler compositions having adsorption values no greater than 80 micromoles/g filler can be used.

Filler (t) at 50% and 70% (w/w) loading met the minimum Barcol hardness level even though its adsorption value was greater than 80 micromoles/g filler. Conversely, filler (g) at 70% (w/w) loading did not meet the minimum Barcol hardness value even though it had an adsorption value less than 80 micromoles/g filler. This demonstrates that the individual screening tests preferably should be used in combination with each other for the best results.

TABLE 4A

| Filler | Γ (μmoles/g) | 50% (w/w) Filler | |
|---|---|---|---|
| | | GYZJ-934-1 | GYZJ-935 |
| (a) | 8.63 | 18 | 82 |
| (b) | 27.33 | 22 | 88 |
| (c) | 7.19 | 22 | 88 |
| (d) | 5.75 | 28 | 82 |
| (e) | 86.29 | No Cure | No Cure |
| (f) | 86.29 | No Cure | No Cure |
| (g) | 11.51 | 22 | 82 |
| (h) | 86.29 | No Cure | No Cure |
| (i) | 8.63 | 8 | 82 |
| (j) | 10.35 | 18 | 88 |
| (k) | 12.94 | 18 | 82 |
| (l) | 10.35 | 22 | 88 |
| (m) | — | No Cure | No Cure |
| (n) | 5.75 | 42 | 98 |
| (o) | 7.19 | 32 | 92 |
| (p) | 86.29 | No Cure | No Cure |
| (q) | 86.29 | No Cure | No Cure |
| (r) | 12.66 | 32 | 92 |
| (s) | 8.92 | 22 | 82 |
| (t) | 86.29 | 22 | 88 |
| (u) | 8.63 | 22 | 88 |
| (v) | — | — | — |
| (w) | 86.29 | — | — |
| (x) | 8.63 | — | — |

TABLE 4B

| Filler | Γ (μmoles/g) | 70% (w/w) Filler | |
|---|---|---|---|
| | | GYZJ-934-1 | GYZJ-935 |
| (a) | 8.63 | 25 | 95 |
| (b) | 27.33 | No Cure | No Cure |
| (c) | 7.19 | 50 | 95 |
| (d) | 5.75 | 25 | 95 |
| (e) | 86.29 | No Cure | No Cure |
| (f) | 86.29 | No Cure | No Cure |
| (g) | 11.51 | 0 | 0 |
| (h) | 86.29 | No Cure | No Cure |

TABLE 4B-continued

| Filler | Γ (μmoles/g) | 70% (w/w) Filler | |
|---|---|---|---|
| | | GYZJ-934-1 | GYZJ-935 |
| (i) | 8.63 | 30 | 95 |
| (j) | 10.35 | 0 | 95 |
| (k) | 12.94 | 5 | 90 |
| (l) | 10.35 | 35 | 95 |
| (m) | — | No Cure | No Cure |
| (n) | 5.75 | 50 | 95 |
| (o) | 7.19 | 40 | 100 |
| (p) | 86.29 | No Cure | No Cure |
| (q) | 86.29 | No Cure | No Cure |
| (r) | 12.66 | 0 | 85 |
| (s) | 8.92 | 20 | 90 |
| (t) | 86.29 | 0 | 90 |
| (u) | 8.63 | 30 | 85 |
| (v) | — | — | No Cure |
| (w) | 86.29 | No Cure | No Cure |
| (x) | 8.63 | 40 | — |

EXAMPLE 3

This example demonstrates that conductivity may be used as a screening test. Conductivity values for test solutions containing filler compositions were determined according to Test Procedure D. Samples for hardness testing were prepared at 50% (w/w) and 70% (w/w) filler loading as described in Example 1. The resin in each case was Resin B2.

Figure 3A:
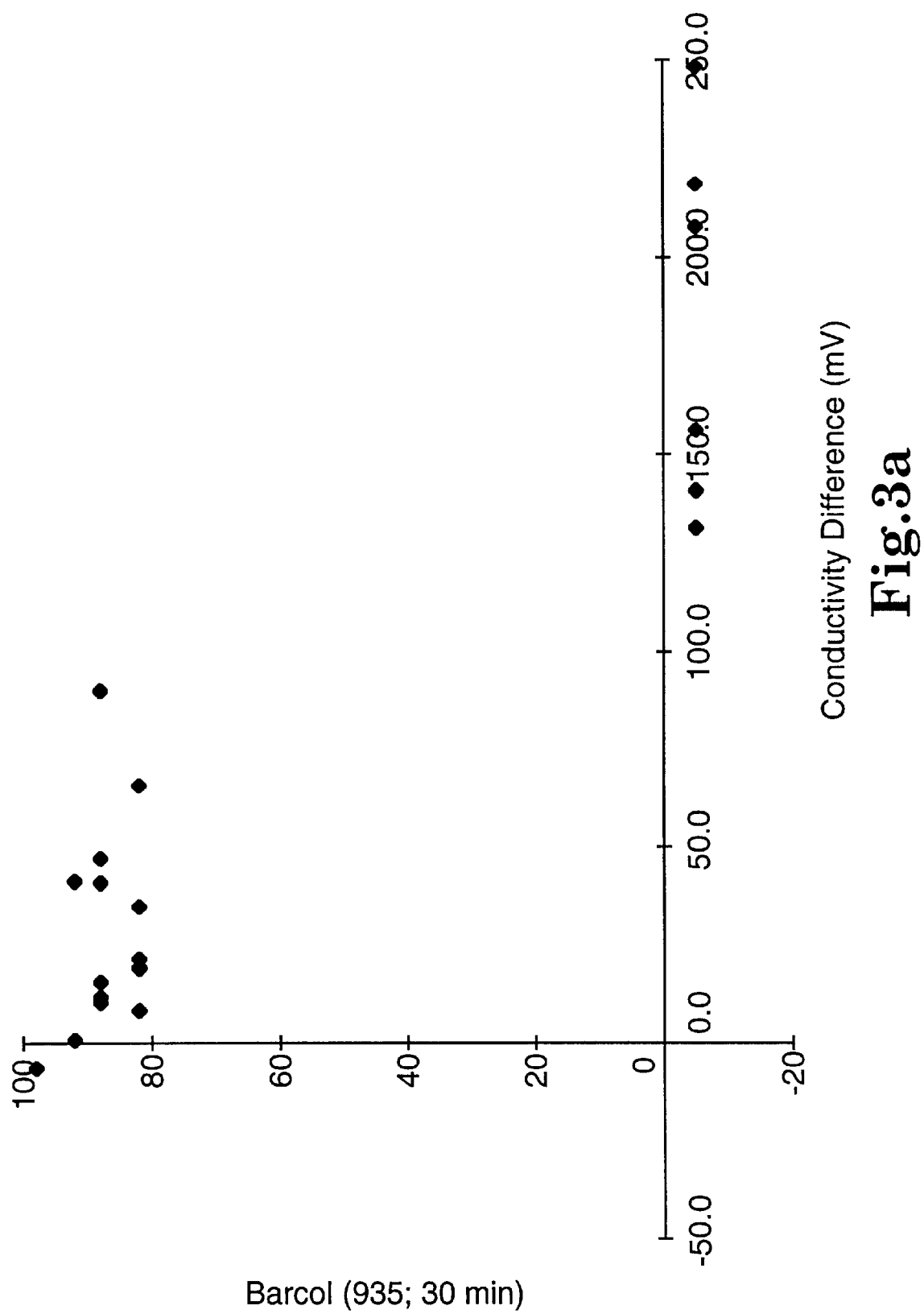
FIGS. 3(a) and 3(b) are plots of Barcol hardness (GYZJ-935 at 30 minutes post-illumination) vs. conductivity change, measured according to Test Procedure D, for composites having filler loadings of 50 and 70% (w/w), respectively.

Hardness was evaluated as described in Example 1. The results are summarized in tabular form in Tables 5A and 5B. The results using the GYZJ-935 meter are also shown graphically in FIGS. 3(a) (50% (w/w) filler loading) and 3(b) (70% (w/w) filler loading). A Barcol value of −5 denotes no cure.

These results demonstrate that, in general, for filler loading of 70% (w/w), fillers causing conductivity changes no greater than 60 mV can be used successfully. In the case of filler loadings of 50% (w/w), fillers causing conductivity changes no greater than 125 mV can be used successfully.

TABLE 5A

| Filler | Conductivity Change (mV) | 50% (w/w) Filler | |
|---|---|---|---|
| | | GYZJ-934-1 | GYZJ-935 |
| (a) | 19.2 | 18 | 82 |
| (b) | 90.2 | 22 | 88 |
| (c) | 10.4 | 22 | 88 |
| (d) | 8.4 | 28 | 82 |
| (e) | 207.5 | No Cure | No Cure |
| (f) | 156.0 | No Cure | No Cure |
| (g) | 65.8 | 22 | 82 |
| (h) | 140.6 | No Cure | No Cure |
| (i) | 19.4 | 8 | 82 |
| (j) | 41.0 | 18 | 88 |
| (k) | 21.5 | 18 | 82 |
| (l) | 47.3 | 22 | 88 |
| (m) | 248.1 | No Cure | No Cure |
| (n) | −6.4 | 42 | 98 |
| (o) | 0.8 | 32 | 92 |
| (p) | 131.3 | No Cure | No Cure |
| (q) | 218.4 | No Cure | No Cure |
| (r) | 41.4 | 32 | 92 |
| (s) | 35.1 | 22 | 82 |
| (t) | 11.9 | 22 | 88 |
| (u) | 15.7 | 22 | 88 |

TABLE 5A-continued

|  | Conductivity | 50% (w/w) Filler | |
| --- | --- | --- | --- |
| Filler | Change (mV) | GYZJ-934-1 | GYZJ-935 |
| (w) | 122 | — | — |
| (x) | −3 | — | — |

TABLE 5B

|  | Conductivity | 70% (w/w) Filler | |
| --- | --- | --- | --- |
| Filler | Change (mV) | GYZJ-934-1 | GYZJ-935 |
| (a) | 19.2 | 25 | 95 |
| (b) | 90.2 | No Cure | No Cure |
| (c) | 10.4 | 50 | 95 |
| (d) | 8.4 | 25 | 95 |
| (e) | 207.5 | No Cure | No Cure |
| (f) | 156.0 | No Cure | No Cure |
| (g) | 65.8 | 0 | 0 |
| (h) | 140.6 | No Cure | No Cure |
| (i) | 19.4 | 30 | 95 |
| (j) | 41.0 | 0 | 95 |
| (k) | 21.5 | 5 | 90 |
| (l) | 47.3 | 35 | 95 |
| (m) | 248.1 | No Cure | No Cure |
| (n) | −6.4 | 50 | 95 |
| (o) | 0.8 | 40 | 100 |
| (p) | 131.3 | No Cure | No Cure |
| (q) | 218.4 | No Cure | No Cure |
| (r) | 41.4 | 0 | 85 |
| (s) | 35.1 | 20 | 90 |
| (t) | 11.9 | 0 | 90 |
| (u) | 15.7 | 30 | 85 |
| (w) | 121.5 | — | No Cure |
| (x) | −3 | 40 | — |

EXAMPLE 4

This example demonstrates that FTIR spectroscopy, using ethyl acetate as a standard, may be used as a screening test in the case of sol-gel-derived fillers. Percent peak height values for test solutions containing filler compositions were determined according to Test Procedure E. Samples for hardness testing were prepared at 50% (w/w) and 70% (w/w) filler as described in Example 1. The resin in each case was Resin B2.

Figure 4A:
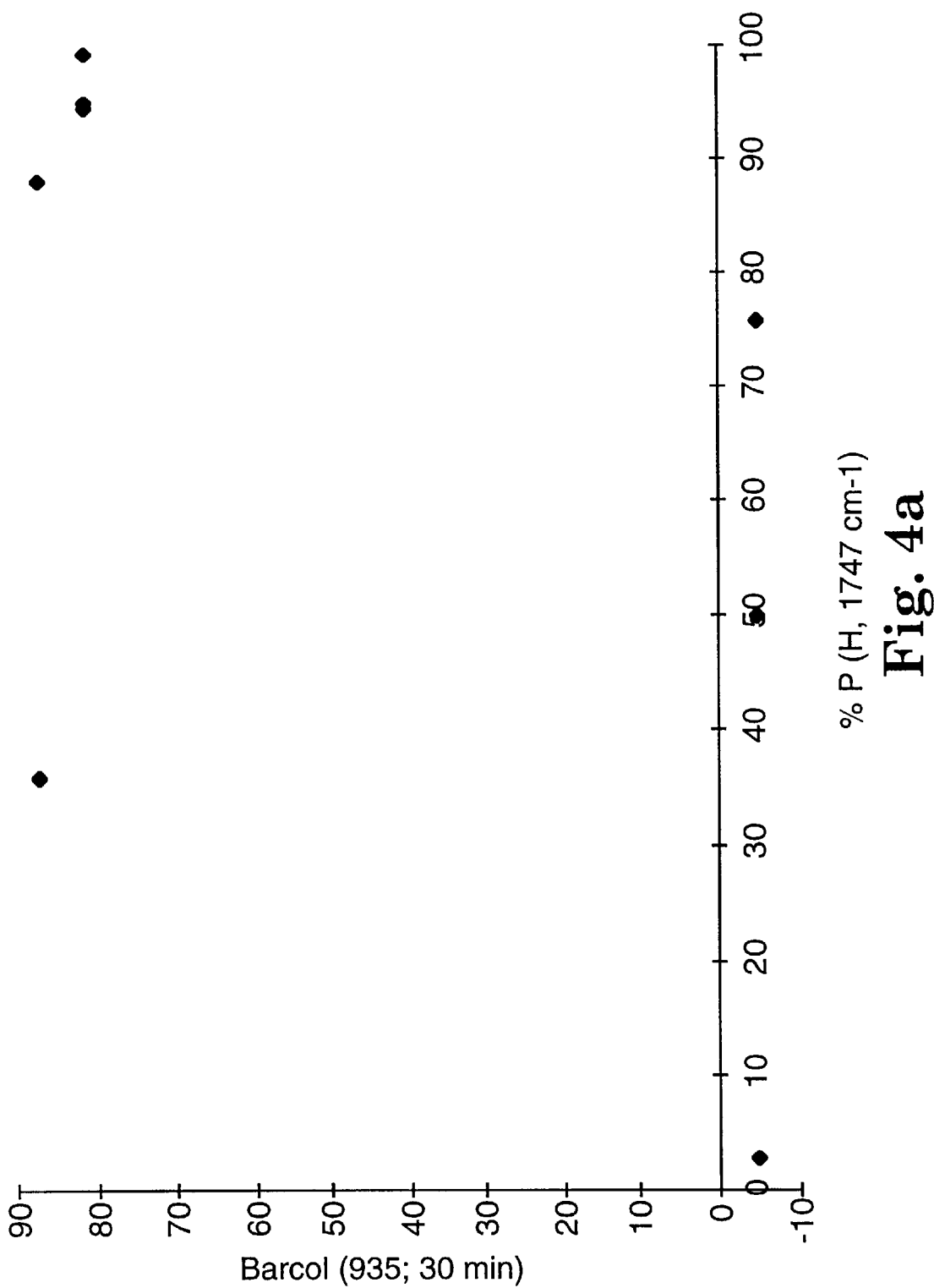
FIGS. 4(a) and 4(b) are plots of Barcol hardness (GYZJ-935 at 30 minutes post-illumination) vs. percent peak height, measured according to Test Procedure E, for composites having filler loadings of 50 and 70% (w/w), respectively.
Figure 4B:
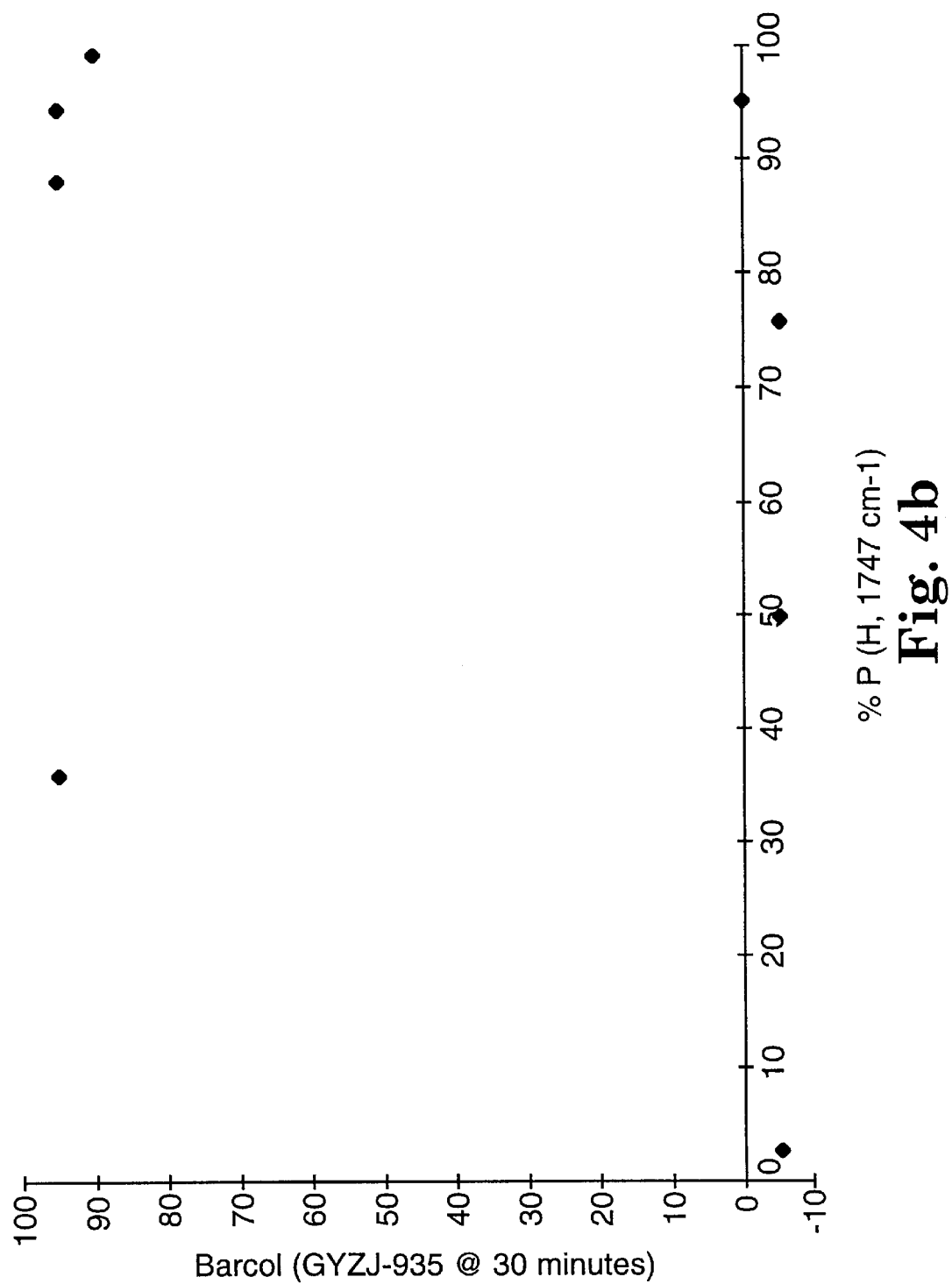

Hardness was evaluated as described in Example 1. The results are summarized in tabular form in Tables 6A and 6B. The results using the GYZJ-935 meter are also shown graphically in FIGS. 4(a) (50% (w/w) filler loading) and 4(b) (70% (w/w) filler loading). A Barcol value of −5 denotes no cure.

The results demonstrate that in general, filler compositions having an FTIR peak height relative to ethyl acetate of greater than 80% can be used successfully.

Filler (j) at both 50% and 70% loading successfully polymerized even though its % peak height value was less than 80%. Conversely, filler (g) at 70% loading did not meet the minimum Barcol hardness value even though its % peak height value was greater than 80%. These results demonstrate that the individual screening tests preferably should be used in combination with each other for the best results.

TABLE 6A

|  | % Peak | 50% (w/w) Filler | |
| --- | --- | --- | --- |
| Filler | Height | GYZJ-934-1 | GYZJ-935 |
| (f) | 75.7 | No Cure | No Cure |
| (g) | 95.1 | 22 | 82 |
| (h) | 49.9 | No Cure | No Cure |
| (i) | 94.6 | 8 | 82 |
| (j) | 35.9 | 18 | 88 |
| (k) | 99.4 | 18 | 82 |
| (l) | 88.2 | 22 | 88 |
| (m) | 2.7 | No Cure | No Cure |

TABLE 6B

|  | % Peak | 70% (w/w) Filler | |
| --- | --- | --- | --- |
| Filler | Height | GYZJ-934-1 | GYZJ-935 |
| (f) | 75.7 | No Cure | No Cure |
| (g) | 95.1 | 0 | 0 |
| (h) | 49.9 | No Cure | No Cure |
| (i) | 94.6 | 30 | 95 |
| (j) | 35.9 | 0 | 95 |
| (k) | 99.4 | 5 | 90 |
| (l) | 88.2 | 35 | 95 |
| (m) | 2.7 | No Cure | No Cure |

EXAMPLES 5–44

These examples demonstrate the successful preparation of a number of cationically polymerized compositions using various radiopacifying filler compositions. The various fillers were prepared as follows:

EXAMPLE 5

The filler sample was a commercially available strontium aluminoborosilicate glass, Raysorb™ T4000 (Ess-Tech, Essington, Pa.).

EXAMPLE 6

The filler sample was a commercially available barium aluminoborosilicate glass, Schott GM-27884 (Schott Glaswerke, Landshut, Germany); the composition reported by the vendor is shown in Table 7.

EXAMPLE 7

The filler sample was prepared by ball milling a commercial barium aluminoborosilicate glass, Corning 7724 (Corning Glass Works, Coming, NY) with alumina media for 3 hours. The milled glass was then heated at 600° C. for 18 h.

EXAMPLE 8

The filler sample was prepared by a conventional melt process.

Appropriate precursors were weighed out to yield the oxide composition shown in Table 7. After blending, the batch was heated to 1400–1500° C. for a sufficient time to assure a homogeneous melt, quenched in water, and dried. The glass frit was then ball milled.

EXAMPLE 9

The filler sample was prepared by milling a glass frit in an alumina mill in a Spex 8000 unit (Spcx Industries, Edison, N.J.) for 10 min. The glass frit was prepared by weighing out appropriate precursors to yield the oxide composition shown in Table 7. After blending, the batch was heated to 1400–1650° C. for a sufficient time to assure a homogeneous melt, quenched in water, and dried.

EXAMPLE 10

The filler sample was prepared by milling a glass frit, prepared as described in Example 9, in an alumina mill in the Spex 8000 for 30 min; the fillers were then sieved with a 400 micrometer nylon screen.

EXAMPLE 11

The filler sample was prepared by milling a glass frit, prepared as described in Example 9, in an alumina mill in the Spex 8000 for 20 min.

EXAMPLE 12

The filler sample was prepared by milling a glass frit, prepared as described above in Example 9, in a ball mill with alumina media for 24 hours; the powder was then heated to 600° C. for 24 hours.

EXAMPLE 13

The filler sample was prepared by milling a glass frit, prepared as described in Example 9, in an alumina mill in the Spex 8000 for 30 min; the fillers were then sieved with a 400 micrometer nylon screen.

EXAMPLE 14

The filler sample was prepared by milling a glass frit, prepared as described in Example 9, in an zirconia mill in the Spex 8000 for 10 min.

EXAMPLE 15

The filler sample was prepared by ball milling a glass frit, prepared as described in Example 9, with alumina media; the mill charge included 600 parts by weight glass frit and 6 parts ethanol.

EXAMPLE 16

The filler sample was prepared by milling a glass frit, prepared as described in Example 9, in an alumina mill in the Spex 8000 for 20 min.

EXAMPLE 17

The filler sample was prepared by ball-milling a glass frit, prepared as described in Example 9, with alumina media for 24 h; the milled filler was then sieved through a 60 micrometer nylon screen.

EXAMPLE 18

21.39 parts by weight of nitric acid was added to 1071.3 parts of colloidal silica sol (Nalco 1042: Nalco Chemical Co.) under vigorous stirring. In 3 0 another vessel, 12.58 parts of nitric acid were added to 616.1 parts zirconyl acetate (Magnesium Elektron, Inc.) under vigorous stirring. Next, the zirconyl acetate preparation was slowly added to the colloidal silica preparation under vigorous stirring. The resulting sol was spray dried in a Niro 3-ft. spray dryer; the resulting powder was fine and free-flowing. The powder was calcined at 500° C. for 4 h, then ball-milled with alumina media; the mill charge included 75 parts calcined material, 3 parts methanol, 1.9 parts benzoic acid, and 1.1 parts deionized water. The filler was then fired at 1 000° C. for 4 h.

EXAMPLE 19

8.9 parts by weight of boric acid was dissolved in 1058 parts by weight of colloidal silica sol (Nalco 1042: Nalco Chemical Co.) under vigorous stirring. In another vessel, 32.23 parts of nitric acid was added to 616.5 parts of zirconyl acetate under vigorous stirring. Next, the zirconyl acetate preparation was slowly added to the colloidal silica preparation under vigorous stirring. The resulting sol was spray dried in a Niro 3-ft. spray dryer; the resulting powder was fine and free-flowing. The powder was calcined at 500° C. for 4 h, then ball-milled with alumina media; the mill charge included 75 parts calcined material, 3 parts methanol, 1.9 parts benzoic acid, and 1.1 parts deionized water. The filler was then fired at 1000° C. for 4 h.

EXAMPLE 20

44.5 parts by weight of boric acid was dissolved in 998 parts by weight of colloidal silica sol (Nalco 1042: Nalco Chemical Co.) under vigorous stirring. In another vessel, 29.03 parts of nitric acid was added to 616.8 parts of zirconyl acetate under vigorous stirring. Next, the zirconyl acetate preparation was slowly added to the colloidal silica preparation under vigorous stirring. The resulting sol was spray dried in a Niro 3-ft. spray dryer; the resulting powder was fine and free-flowing. The powder was calcined at 500° C. for 4 h, then ball-milled with alumina media; the mill charge included 75 parts calcined material, 3 parts methanol, 1.9 parts benzoic acid, and 1.1 parts deionized water. The filler was then fired at 900° C. for 4 h. A vial of the compounded sol was stored under ambient conditions; the sol displayed no gelling or precipitation after 2.5 years.

EXAMPLE 21

1.33 parts by weight of boric acid (33906-7: Aldrich Chemical Company, Inc., Milwaukee) were added to 29.9 parts of colloidal silica sol (1042: Nalco Chemical Company, Naperville) under vigorous stirring. After addition of 13.2 parts deionized water, stirring was continued until the boric acid was fully dissolved. In another vessel 18.63 parts of zirconyl acetate (Magnesium Elektron, Inc.) was charged; under vigorous stirring 0.97 parts ACS grade nitric acid was added to the zirconyl acetate. The colloidal silica preparation was added to the zirconyl acetate preparation under vigorous stirring; stirring was continued for 1 hr. The sol was spray dried in a 3-ft. Niro spray drying unit with a rotary atomizer set at 20,000 RPM; the resulting powder was fine and free-flowing. The spray dried powder was loaded into ceramic saggers and calcined in air in an electric furnace (Cress Mfg. Company, El Monte, Calif.) according to the profile: ramp to 200° C., soak for 1 hr, ramp to 550° C., hold for 4 hr, cool to room temperature. The powder was then ball-milled with ¼" alumina media for 65 hr; the charge included 130 parts by weight powder, 3 parts benzoic acid, 5 parts methanol, and 2 parts deionized water. After blending in a V-blender (Patterson-Kelly) for 30 min, the powder was loaded into ceramic saggers and fired in air in an electric furnace (ramp to 900° C., hold for 12 hr, cool to room temperature). The powder was then ball-milled for 24 hr with ¼" alumina media; the charge included 400 parts by weight of powder, 4 parts of ethanol, and 1 part of deionized water.

EXAMPLE 22

18.59 parts by weight of nitric acid was added to 856.3 parts deionized water; this solution was then added to 1071.3 parts of colloidal silica sol (Nalco 1042: Nalco Chemical Co.) under vigorous stirring. 88.1 parts of boric acid was then added under vigorous stirring. In another vessel 12.58 parts of nitric acid were added to 616.1 parts zirconyl acetate (Magnesium Elektron, Inc.) under vigorous stirring. Next, the zirconyl acetate preparation was slowly added to the colloidal silica preparation under vigorous stirring. The resulting sol was spray dried in a Niro 3-ft. spray dryer; the resulting powder was fine and free-flowing. The powder was calcined at 500° C. for 4 h, then ball-milled with alumina media; the mill charge included 75 parts calcined material, 3 parts methanol, 1.9 parts benzoic acid, and 1.1 parts deionized water. The filler was then fired at 800° C. for 4 h. A vial of the compounded sol was stored under ambient conditions; the sol displayed no gelling or precipitation after 2.5 years.

EXAMPLE 23

7.0 parts by weight of nitric acid was added to 1414 parts deionized water; this solution was then added to 389 parts of colloidal silica sol (Nalco 1042: Nalco Chemical Co.) under vigorous stirring. 88.1 parts of boric acid was then added under vigorous stirring. In another vessel 6.0 parts of nitric acid were added to 308 parts zirconyl acetate (Magnesium Elektron, Inc.) under vigorous stirring. Next, the zirconyl acetate preparation was slowly added to the colloidal silica preparation under vigorous stirring. The resulting sol was spray dried in a Niro 3-ft. spray dryer; the resulting powder was fine and free-flowing. The powder was calcined at 500° C. for 4 h, then ball-milled with alumina media; the mill charge included 75 parts calcined material, 3 parts methanol, 1.9 parts benzoic acid, and 1.1 parts deionized water. A vial of the compounded sol was stored under ambient conditions; the sol displayed no gelling or precipitation after 2.5 years.

EXAMPLE 24

11 parts by weight of AFA was charged to a vessel. Under vigorous stirring were then added 64.5 parts of a solution of 23.3 parts boric acid dissolved in 466.6 parts deionized water, 21.4 parts zirconyl acetate (Magnesium Elektron, Inc.), 36.9 parts of colloidal silica sol (1034A: Nalco Chemical Co.), and 16.3 parts glacial acetic acid. The sol was stirred for 3 days, then spray dried in a Büchi spray dryer. The powder was calcined at 500° C. for 4 h, then fired at 1 050° C. for 2 h.

EXAMPLE 25

140 parts by weight of lanthanum nitrate hexahydrate (12915: Alfa Aesar, Ward Hill, Mass.) was dissolved in 120 parts deionized water. 97 parts of colloidal silica sol (1034A: Nalco Chemical Co.) were added to 83.9 parts of the lanthanum nitrate solution under vigorous stirring. The resulting sol was poured into a Pyrex™ tray and placed in an oven at 55° C. for 2 days; the dried gel was then milled in an alumina mill in a Spex 8000 unit (Spex Industries, Edison, N.J.) for 5 min. The powder was then fired at 1050° C. for 2 h.

EXAMPLE 26

889 parts by weight of lanthanum nitrate hexahydrate was dissolved in 902 parts of deionized water. 34.2 parts of colloidal silica sol (1034A: Nalco Chemical Co.) was added to 43.2 parts of the lanthanum nitrate solution under vigorous stirring. The resulting sol was poured into a Pyrex M tray and dried at 55° C. to a coarse particulate gel. The dried gel was calcined at 550° C. for 3 h, manually crushed to a powder in an alumina mortar and pestle, then fired at 1050° C. for 2 h.

EXAMPLE 27

965 parts by weight of AFA was charged to a beaker; under vigorous stirring were then added 158 parts of a solution of 889 parts lanthanum nitrate hexahydrate in 902 parts deionized water, followed by 383 parts of colloidal silica sol (1034A: Nalco Chemical Co.). The resulting sol was spray dried in a Niro 3-ft. spray dryer. The resulting powder was calcined at 550° C. for 4 h, then ball milled with ¼" alumina media; the charge included 130 parts by weight powder, 3 parts benzoic acid, 5 parts methanol, and 2 parts deionized water. The filler was fired at 1000° C. for 4 h. The fired filler was ball milled with ½" alumina media; the charge included 130 parts of filler, 5.2 parts ethanol, and 1.3 parts water.

EXAMPLE 28

128.4 parts by weight of deionized water was added to 99.5 parts of colloidal silica sol (1034A: Nalco Chemical Co.) under vigorous stirring and low heat; 20.0 parts of boric acid (339067: Aldrich Chemical Co.) was added; 113.4 parts of deionized water was added. Vigorous stirring continued throughout until all powder was dissolved. In a separate vessel 674.3 parts of lanthanum nitrate hexahydrate was dissolved in 809 parts deionized water; next, 29.4 parts of the lanthanum nitrate solution was added to the colloidal silica preparation. The resulting sol was diluted by 1 part by weight sol per 2 parts deionized water, and then spray dried on a Niro 3-foot spray dryer. After calcining at 500° C. for 4 h, the powder was fired at 850° C. for 2 h; the resulting powder was free flowing.

EXAMPLE 29

100 parts by weight of deionized water was added to 111.7 parts of colloidal silica sol (1034A: Nalco Chemical Co.) under vigorous stirring and low heat; 8.9 parts of boric acid (339067: Aldrich Chemical Co.) was added; vigorous stirring was continued until all powder was dissolved. In a separate vessel 674.3 parts of lanthanum nitrate hexahydrate was dissolved in 809 parts deionized water; next, 41.0 parts of the lanthanum nitrate solution was added to the colloidal silica preparation. The resulting sol was diluted by 1 part by weight sol per 2 parts deionized water, and then spray dried on a Niro 3-foot spray dryer. After calcining at 500° C. for 4 h, the powder was fired at 850° C. for 2 h; the resulting powder was free flowing.

EXAMPLE 30

The filler sample was prepared identically to the filler sample of Example 29 except that the firing temperature was 1050° C. instead of 850° C.

EXAMPLE 31

2.7 parts of boric acid (339067: Aldrich Chemical Co.) was added to 111.7 parts of colloidal silica sol (1034A: Nalco Chemical Co.) under vigorous stirring and low heat until all powder was dissolved. In a separate vessel 674.3 parts of lanthanum nitrate hexahydrate was dissolved in 809 parts deionized water; next, 48.0 parts of the lanthanum nitrate solution was added to the colloidal silica preparation. The resulting sol was diluted by 1 part by weight sol per 2 parts deionized water, and then spray dried on a Niro 3-foot spray dryer. After calcining at 500° C. for 4 h, the powder was fired at 850° C. for 2 h; the resulting powder was free flowing.

EXAMPLE 32

The filler sample was prepared identically to the filler sample of Example 31 except that the firing temperature was 1050° C. instead of 850° C.

EXAMPLE 33

The filler sample was prepared identically to the filler sample of Example 31 except that the firing temperature was 1200° C. instead of 850° C.

EXAMPLE 34

4.43 parts by weight of boric acid (339067: Aldrich Chemical Co.) was dissolved fully in 97 parts of colloidal silica sol (1034A: Nalco Chemical Co.) under vigorous stirring and low heat. In another vessel 140 parts by weight of lanthanum nitrate hexahydrate (12915: Alfa Aesar, Ward Hill, Mass.) was dissolved in 120 parts deionized water. 70.9 parts of the lanthanum nitrate solution was added to t he colloidal silica preparation under low heat and vigorous stirring. About 25 ml of the resulting sol was poured into a Pyrex™ beaker and heated in a microwave oven (Model R-9H83: Sharp Electronics Corp., Mahwah, N.J.) for 9 min; the result was an opaque, moist gel. This gel was calcined at 550° C. for 2.5 h, then milled in an alumina mill in the Spex 8000 for 2 min.

EXAMPLE 35

Sol prepared identically to the filler sample of Example 34 was poured into a tray and dried at 60° C. for three days; the dried gel was then milled in an alumina mill in the Spex 8000 for 20 min. The milled powder was heated to 500° C. for 2 h, then heated to 900° C. for 4 h.

EXAMPLE 36

173 parts by weight of AFA was charged to a vessel. Under vigorous stirring, the following ingredients were added, one at a time: 53 parts colloidal silica sol (1034A: Nalco Chemical Co.), 263.3 parts of a solution of 674.3 parts lanthanum nitrate hexahydrate and 809.4 parts deionized water, 28.4 parts boric acid. Stirring was continued until the powder was completely dissolved. The sol was spray dried in a Buchi spray dryer. The resulting powder was calcined at 500° C. for 45 min, then at 800° C. for about 14 h. The powder was fired at 850° C. for 6 h.

EXAMPLE 37

Spray dried powder prepared as described in Example 38 (below) was calcined at 500° C. for 2:45 h, and then milled in an alumina mill in a Spex 8000 unit (Spex Industries, Edison, N.J.) for 5 min.

EXAMPLE 38

86.5 parts by weight of AFA was charged to a vessel. Under vigorous stirring, the following ingredients were added, one at a time: 33.9 parts colloidal silica sol (1034A: Nalco Chemical Co.), 131.6 parts of a solution of 674.3 parts lanthanum nitrate hexahydrate and 809.4 parts deionized water, 14.2 parts boric acid. Stirring was continued until the powder was completely dissolved. The sol was spray dried in a Buchi spray dryer. The resulting powder was calcined at 500° C. for 45 min, then at 800° C. for about 14 h. The powder was fired at 850° C. for 6 h.

EXAMPLE 39

Under vigorous stirring, 38.4 parts of a solution of yttrium nitrate hexahydrate in deionized water yielding 15.7 wt % of yttrium oxide was added to 26.6 parts of colloidal silica sol sol (1034A: Nalco Chemical Co.); several drops of nitric acid was added to reduce the pH from about 4–5 to 0–0.5. The sol was poured into a Pyrex™ beaker, then heated in a microwave oven for 14 min. The resulting dried gel was fired at 1000° C. for 2 h, then ground manually in an alumina mortar and pestle to a powder.

EXAMPLE 40

48.7 parts by weight of AFA was charged to a vessel. Under vigorous stirring, 28.8 parts of a solution of yttrium nitrate hexahydrate in deionized water, yielding 15.7 wt % of yttrium oxide, was added to 17.9 parts of colloidal silica sol sol (1034A: Nalco Chemical Co). The sol was poured into a Pyrex™ beaker, then heated in a microwave oven for 19 min. The resulting dried gel was fired at 1000° C. for 2 h, then ground manually in an alumina mortar and pestle to a powder.

EXAMPLE 41

Approximately 4.86 kg of Nalco 2326 silica sol (a silica sol of 14.5 wt % solids, pH of 9.0, ammonium ion stabilized) was mixed with 6.02 kg of water.

To this was added a mixture of 1.34 kg Nyacol 10/20 Zirconia sol (a zirconia sol of 20 wt % solids, pH of 0.5, nitrate ion stabilized) with 1.48 kg of water containing 30 g of boric acid pre-dissolved in it. This resulted in a sol which, on a solids weight basis, is approximately 70% silica, 27% zirconia, and 3% boric acid.

This sol was subsequently spray dried, at 30,000 R.P.M. on a Niro 3 ft. spray dryer, an inlet temperature of approximately 200° C., and an outlet temperature of 100° C. The resulting powder was then fired at 1000° C. for 6 hours.

EXAMPLE 42

Approximately 5.03 kg of Nalco 2326 silica sol (a silica sol of 14.5 wt % solids, pH of 9.0, ammonium ion stabilized) was mixed with 5.06 kg of water. To this was added a mixture of 1.34 kg Nyacol 10/20 Zirconia sol (a zirconia sol of 20 wt % solids, pH of 0.5, nitrate ion stabilized) with 1.36 kg of water. This resulted in a sol which, on a solids weight basis, is approximately 73% silica and 27% zirconia.

This sol was subsequently spray dried, at 30,000 R.P.M., on a Niro 3 ft. spray dryer an inlet temperature of approximately 200° C., and an outlet temperature of 100° C. The resulting powder was then fired at 1000° C. for 6 hours.

When evaluated according to Test Procedure E, the filler exhibited a % peak height of 100.

EXAMPLE 43

Nyacol 10/20 Zirconia sol (a zirconia sol of 20 wt % solids, pH of 0.5, nitrate ion stabilized) was dried in an oven at 140° C. overnight to remove water. The sample was then crushed by hand using a mortar & pestle to break up loose agglomerates. The resulting powder was fired at 1000° C. to remove any residual nitrates. When evaluated according to Test Procedure E, the filler exhibited a % peak height of 100.

EXAMPLE 44

The filler sample was prepared identically as described in Example except that the sample was fired at 800° C. for 4 hours.

The chemical compositions of the fillers used in Examples 5–44 are summarized below in Table 7. All amounts given are in weight %.

TABLE 7

| Example | Al2O3 | B2O3 | BaO | La2O3 | SiO2 | Y2O3 | ZnO | ZrO2 | Other |
|---|---|---|---|---|---|---|---|---|---|
| 5 | — | — | — | — | — | — | — | — | — |
| 6 | 10 | 10 | 25 | — | 55 | — | — | — | — |
| 7 | — | — | — | — | — | — | — | — | — |
| 8 | 15 | 9 | 4.5 | — | 50 | — | 21 | — | 0.5F |
| 9 | 14.65 | 9.09 | 4.55 | — | 50.5 | — | 21.21 | — | — |
| 10 | 14.5 | 9 | — | 4.5 | 51 | — | 21 | — | — |
| 11 | 10 | 30 | — | — | 30 | — | — | — | 30 Ta2O5 |
| 12 | 20 | 25 | — | — | 30 | — | — | — | 25 Yb2O3 |
| 13 | 10 | 20 | — | 40 | 30 | — | — | — | — |
| 14 | 16 | 16 | — | 45 | 23 | — | — | — | — |
| 15 | 20 | 20 | — | 30 | 30 | — | — | — | — |
| 16 | 35.7 | — | — | 12.3 | 52 | — | — | — | — |
| 17 | 20 | — | — | 25 | — | — | — | — | 55 P2O5 |
| 18 | — | — | — | — | 72.8 | — | — | 27.2 | — |
| 19 | — | 1 | — | — | 71.8 | — | — | 27.2 | — |
| 20 | — | 5 | — | — | 67.8 | — | — | 27.2 | — |
| 21 | — | 5 | — | — | 67.8 | — | — | 27.2 | — |
| 22 | — | 10 | — | — | 52.8 | — | — | 27.2 | — |
| 23 | — | 20 | — | — | 52.8 | — | — | 27.2 | — |
| 24 | — | — | — | — | — | — | — | — | — |
| 25 | — | — | — | 34 | 66 | — | — | — | — |
| 26 | — | — | — | 42 | 58 | — | — | — | — |
| 27 | 35.7 | — | — | 12.3 | 52 | — | — | — | — |
| 28 | — | 23 | — | 10 | 67.5 | — | — | — | — |
| 29 | — | 10 | — | 14 | 76 | — | — | — | — |
| 30 | — | 10 | — | 14 | 76 | — | — | — | — |
| 31 | — | 3 | — | 16.4 | 80.6 | — | — | — | — |
| 32 | — | 3 | — | 16.4 | 80.6 | — | — | — | — |
| 33 | — | 3 | — | 16.4 | 80.6 | — | — | — | — |
| 34 | — | 5 | — | 29 | 66 | — | — | — | — |
| 35 | — | 5 | — | 29 | 66 | — | — | — | — |
| 36 | 16 | 16 | — | 45 | 18 | — | — | — | 5 CeO2 |
| 37 | 16 | 16 | — | 45 | 23 | — | — | — | — |
| 38 | 16 | 16 | — | 45 | 23 | — | — | — | — |
| 39 | — | — | — | — | 60 | 40 | — | — | — |
| 40 | 30 | — | — | — | 40 | 30 | — | — | — |
| 41 | — | 0.75 | — | — | 71.6 | — | — | 27.65 | — |
| 42 | — | — | — | — | 73 | — | — | 27 | — |
| 43 | — | — | — | — | — | — | — | — | — |
| 44 | — | 5 | — | — | 67.8 | — | — | 27.2 | — |

The fillers used in Examples 5–44 were also characterized according Test Procedures H–M. The results are summarized below in Table 8.

The designation "—" means not tested.

TABLE 8

| Exam. | $n_D$ | XRD | Fluorescence | BET (m²/g) | Part. Size (μm) | Sp. gravity (g/cc) |
|---|---|---|---|---|---|---|
| 5 | — | Am + very weak unid. Ph. | W/B | 2.27 | 11.6 | — |
| 6 | 1.528 | Am | N | 8.91 | 1.22 | — |
| 7 | 1.545 | — | N | 1.41 | 8.28 | — |
| 8 | 1.549 | — | — | — | — | — |
| 9 | — | — | B/W | — | — | — |
| 10 | — | — | — | 0.51 | 18.2 | — |
| 11 | 1.514 | — | N | 0.17 | — | — |
| 12 | — | — | — | — | — | — |
| 13 | 1.614 | — | B/W | 0.35 | 53.17 | — |
| 14 | 1.644 | — | Y | 0.28 | 14.76 | — |
| 15 | 1.585 | — | N | 2.2 | 2.45 | — |
| 16 | 1.528 | — | — | — | — | — |
| 17 | — | — | N | — | — | — |
| 18 | 1.540 | — | N | 34.3 | — | 2.742 |
| 19 | 1.542 | — | N | 6.1 | — | 2.708 |
| 20 | — | Am + ZrO2 (T, pc) | — | 5.8 | — | 2.690 |
| 21 | 1.542 | — | N | 2.36 | 21 | — |
| 22 | 1.538 | — | N | 7.1 | — | 2.684 |
| 23 | 1.536 | — | Y | 86 | — | 2.51 |
| 24 | 1.526 | Am + ZrO2C | — | 20.5 | — | — |
| 25 | 1.522 | — | — | 1.55 | — | — |
| 26 | — | Unid. Cry. Ph. | — | 10.36 | — | — |
| 27 | — | — | — | 5.42 | 0.86 | — |
| 28 | 1.487 | Am | — | 18.92 | — | — |
| 29 | 1.475 | Am + very weak unid. Ph. | — | 53.07 | — | — |
| 30 | 1.486 | Am | — | 16.18 | — | — |
| 31 | 1.500 | Am | — | 13.99 | — | — |
| 32 | 1.504 | Am + very weak, unid. Ph. | — | 49.01 | — | — |
| 33 | 1.505 | α-Cr + Unid. Cry. Ph. | N | 0.11 | — | — |
| 34 | — | — | — | 50.84 | — | — |
| 35 | — | — | Y | 2.85 | — | — |
| 36 | — | — | — | 1.19 | — | — |
| 37 | 1.644 | — | — | 31.08 | — | — |
| 38 | 1.644 | — | — | 2.4 | — | — |
| 39 | 1.578 | AM | — | 58.58 | — | — |
| 40 | 1.532 | AM | — | 0.49 | — | — |
| 41 | — | — | — | <1 | 11.63 | — |
| 42 | — | — | — | <1 | 13.45 | — |

TABLE 8-continued

| Exam. | $n_D$ | XRD | Fluor- escence | BET $(m^2/g)$ | Part. Size ($\mu$m) | Sp. gravity (g/cc) |
|---|---|---|---|---|---|---|
| 43 | — | — | — | — | 5 nm | — |
| 44 | — | Am + ZrO2 (tet/pc) | — | 34.6 | 2.8 | 2.691 |

Each filler was used to prepare a composite as described in Example The resin used in each example was Resin B1, with the exception of Examples 11 (Resin B4), 12 (Resin B 3), and 41–43 (Resin B4).

The hardness of each composite was evaluated according to Test Procedure A at 30 minutes post-cure using the GYZJ-934-1 meter. The results are reported in Table 9. An asterisk means that the Barcol value was measured immediately after removing the visible light source.

TABLE 9

| Example | Barcol | % Filler (w/w) |
|---|---|---|
| 5 | 40 | 70 |
| 6 | 45 | 40 |
| 7 | 40 | 70 |
| 8* | 40 | 70 |
| 9* | 30 | 40 |
| 10 | 55 | 70 |
| 11 | 58 | 70 |
| 12 | 48 | 70 |
| 13 | 55 | 70 |
| 14 | 55 | 70 |
| 15 | — | 70 |
| 16 | 55 | 70 |
| 17* | 38 | 70 |
| 18 | 55 | 40 |
| 19 | 55 | 50 |
| 20 | 55 | 70 |
| 21 | 50 | 70 |
| 22 | 40 | 60 |
| 23 | 40 | 40 |
| 24* | 30 | 57 |
| 25* | 45 | 70 |
| 26* | 45 | 70 |
| 27 | 45 | 70 |
| 28* | 50 | 40 |
| 29* | 50 | 40 |
| 30* | 50 | 40 |
| 31* | 50 | 40 |
| 32* | 40 | 40 |
| 33* | 10 | 70 |
| 34* | 35 | 40 |
| 35* | 45 | 70 |
| 36* | 25 | 40 |
| 37* | 45 | 70 |
| 38* | 30 | 40 |
| 39* | 15 | 40 |
| 40* | 15 | 40 |
| 41 | 60 | 70 |
| 42 | 60 | 70 |
| 43 | — | 70 |
| 44 | 55 | 60 |

EXAMPLES 45–49

These examples describe the successful preparation of a number of cationically polymerized compositions containing various radiopacifying filler blends. The various filler blends were prepared as follows:

EXAMPLE 45

The filler sample consisted of a blend of 5 parts by weight of quartz filler (filler (n)) and 2 parts of tin difluoride (Aldrich Chemical Co.).

EXAMPLE 46

The filler sample consisted of a blend of 5 parts by weight of quartz filler (filler (n)) and 2 parts of zinc difluoride (Aldrich Chemical Co.).

EXAMPLE 47

The filler sample consisted of a blend of 5 parts by weight of quartz filler (filler (n)) and 2 parts of bismuth oxide (Aldrich Chemical Co.).

EXAMPLE 48

The filler sample consisted of a blend of 14.6 parts quartz filler (filler (n)) and 5.4 parts of colloidal zirconia filler.

EXAMPLE 49

The filler sample consisted of a blend of 6 parts by weight of quartz filler (filler (n)) and 10 parts of zinc difluoride (Aldrich Chemical Co.).

Each filler blend was used to prepare a composite according to the general procedure described above.

The hardness of each composite was evaluated according to Test Procedure A at 30 minutes post-cure using the GYZJ-934-1 meter. The results are reported in Table 10.

TABLE 10

| Example | Barcol | Filler % (w/w) | Resin |
|---|---|---|---|
| 45 | 52 | 70 | B4 |
| 46 | 82 | 70 | B4 |
| 47 | 47 | 70 | B4 |
| 48 | 60 | 70 | B2 |
| 49 | 72 | 70 | B4 |

EXAMPLES 50–52

These examples describe the preparation of radiopaque composites using a number of different cationic polymerization initiators with UV light and heat. Each composite was prepared using Stock A1. Three different photoinitiators were used. The amount of photoinitiator in each case was 2% (w/w). The filler in each case was filler (a). The filler loading in each case was 50% (w/w). Initiation was accomplished using a combination of ultraviolet radiation (supplied by a Fusion D lamp from Fusion Systems) and heat (100° C. for 10 minutes). The total UV irradiation energy was approximately 1500 mJ/cm$^2$.

The hardness of each composite was evaluated according to Test Procedure A using the GYZJ-934-1 meter. The results are shown in Table 11. The results demonstrate that radiopaque composites can be successfully prepared via cationic polymerization using a variety of cationic initiators.

TABLE 11

| EXAMPLE | INITIATOR | BARCOL |
|---|---|---|
| 50 | 2% CD1012 | 50 |
| 51 | 2% CD1010 | 55 |
| 52 | 2% COM | 55 |

CD1012 is diaryl hexafluoroantimonate (Sartomer).
CD1010 is triaryl sulfonium hexafluoroantimonate (Sartomer).
COM is cyclopentadienyl iron (II) xylene hexafluoroantimonate (3M).

EXAMPLE 53

This example describes the preparation of composites using a hybrid resin system featuring cationically active functional groups and free radically active functional groups. The composites were prepared as described in Example 1. The resin was an 80:20:30 blend of UVR-6105 epoxy resin, polytetrahydrofuran 250 (M.W.=250 Da), and TMPTA (trifunctional acrylate).

The resin contained 1.25% (w/w) CD 1012 iodonium salt and 0.5% (w/w) CPQ visible light sensitizer.

The hardness of each composite was evaluated according to Test Procedure A using the GYZJ-934-1 meter. The results are shown in Table 12. In contrast, when combined with only epoxy resin, both fillers resulted in composites that failed to cure. The results demonstrate that radiopaque composites can be successfully prepared using hybrid resin systems.

TABLE 12

| FILLER | BARCOL | FILLER % (w/w) |
|---|---|---|
| (b) | 65 | 70 |
| (f) | 80 | 70 |

EXAMPLES 54–60

These examples demonstrate that coated radiopacifying fillers featuring a core and a coating having a chemical composition different from that of the core can be used to prepare composites from cationically polymerizable resins.

The coated fillers were prepared as follows:

EXAMPLE 54

This filler featured a quartz core with a zirconia coating. Quartz filler (filler (n)) was dispersed in a colloidal zirconia sol (Nyacol ZRYS-4) under vigorous stirring such that the oxide composition yielded was approximately 10 wt % zirconia and 90 wt % quartz. The resulting slurry was spray dried and then fired at 1000° C. for 6 h. The resulting coated filler particles had a B.E.T. surface area, measured according to Test Procedure H, of 0.75 $m^2/g$.

EXAMPLE 55

This filler featured a quartz core with a zirconia coating. The filler was prepared following the procedure of Example 54 except that the firing step was omitted. The resulting coated filler particles had a B.E.T. surface area, measured according to Test Procedure H, of 4.04 $m^2/g$.

EXAMPLE 56

This filler featured a quartz core with a zirconia coating. The filler was prepared following the procedure of Example 54 except that the oxide composition was approximately 50 wt % zirconia and 50 wt % quartz. The resulting coated filler particles had a B.E.T. surface area, measured according to Test Procedure H, of 0.75 $m^2/g$.

EXAMPLE 57

This filler featured a zirconia-silica core with a boria-silica coating. Zirconia-silica filler was made according to the procedure used to prepare filler (f), except that the steps after the first ball milling were omitted. Under vigorous stirring, 800 parts by weight of this zirconia-silica filler was slurried into 16000 parts deionized water and 200 parts of a sol containing 532.9 parts of boric acid, 16765 parts colloidal silica sol (1042: Nalco Chemical Co.), and 3131 parts deionized water. The coating thus applied had a nominal composition of 5 wt % $B_2O_3$ and 95 wt % $SiO_2$. The resulting suspension was spray dried in a Niro spray dryer. The resulting powder was then fired at 850° C. for 6 h. The resulting coated filler particles had a B.E.T. surface area, measured according to Test Procedure H, of 27.98 $m^2/g$.

EXAMPLE 58

This filler featured a zirconia-silica core with a boria coating. The filler was prepared following the procedure of Example 57, except that the firing temperature was 950° C. instead of 850° C. The resulting coated filler particles had a B.E.T. surface area, measured according to Test Procedure H, of 2.63 $m^2/g$.

EXAMPLE 59

This filler featured an inorganic radiopaque zirconia-silica filler dispersed in a cured methacrylate matrix. One syringe of 3M™ Restorative Z100™ Incisal Paste was dispensed between two sheets of plastic film, squeezed to a thickness less than 1 mm, light cured in a Kulzer Dentacolor XS unit for 90 s, and milled in an alumina mill in a Spex 8000 unit for 2 min. The B.E.T. surface area of the resulting coated filler particles was not measured.

EXAMPLE 60

This filler featured an epoxy resin coating on a zirconia-:silica sol gel filler core. A blend of Epon 825 (80 parts), polytetrahydrofuran 250 (20 parts), 1.25% (w/w) CD1012, and 0.5% (w/w) CPQ was magnetically coated onto the surface of a zirconia:silica sol gel filler prepared according to the procedure used to prepare filler (f) except that all steps following the first ball milling were omitted. Magnetic coating was performed following the procedure described in WO97/07900. The coated particles were irradiated under a Sylvania UV lamp for 1 hour (600 $mJ/cm^2$) in order to cure the resin onto the surface of the particle.

Composites were prepared following the procedure described in Example 1. The hardness of each composite was evaluated according to Test Procedure A using the GYZJ-934-1 meter. The results are reported in Table 13. The asterisk means that hardness was evaluated using the GYZJ-935 meter.

TABLE 13

| Example | Barcol | Filler % (w/w) | Resin |
|---|---|---|---|
| 54 | 55 | 70 | B1 |
| 55 | 30 | 70 | B1 |
| 56 | 55 | 40 | B1 |
| 57 | 48 | 50 | B1 |
| 58 | 50 | 70 | B3 |
| 59 | 43 | 60 | B4 |
| 60 | 63* | 30 | B1 |

The results shown in Table 13 demonstrate that coated fillers featuring (a) a radiolucent core and a radiopacifying coating or (b) a radiopacifying core and a radiolucent coating can be used successfully to prepare composites using cationically polymerizable resins.

EXAMPLE 61

This example demonstrates that composites having good depth of cure can be prepared using cationically polymerizable resins and radiopacifying fillers.

Each filler was used to prepare a composite as described in Example 1. Each composite featured a filler loading of 70% (w/w) filler. The polymerizable composition used in each composite was Resin B4.

The depth of cure was evaluated for each composite according to Test Procedure F at depths ranging from 0 mm to 8 mm. The results, in the form of Barcol hardness values measured using the GYZJ-934-1 meter, are reported in Table 14. The designation "—" means not tested.

TABLE 14

| Filler | 0 mm | 2 mm | 3 mm | 4 mm | 5 mm | 6 mm | 7 mm | 8 mm |
|---|---|---|---|---|---|---|---|---|
| (a) | 60 | 60 | 60 | 55 | 40 | 40 | 40 | 40 |
| Ex. 15 | 60 | 40 | 40 | 35 | 28 | 28 | no cure | no cure |
| Ex. 42 | 60 | 60 | 60 | 50 | 60 | 60 | 50 | 45 |
| Ex. 21 | — | — | — | — | — | — | — | 10 |

The results shown in Table 14 demonstrate that depths of cure up to 8 mm can be achieved using radiopacifying fillers.

EXAMPLES 62–64 AND COMP. EX. A

These examples demonstrate that useful dental composites can be prepared using radiopacifying fillers and cationically polymerizable resins. The fillers were prepared as follows.

Comparative Example A

Approximately 30 ml of a solution containing 1 part ethanol and 1 part distilled water was weighed into a polyethylene beaker. Trifluoroacetic acid (Aldrich Chem. Co., Milwaukee, Wis.) was added to adjust the pH to 4.5±0.1. 1.43 parts by weight of 3-glycidoxypropyltrimethoxysilane (G6720: United Chemical Technologies, Inc., Bristol, Pa.) was slowly added while stirring with a teflon coated magnetic stir bar. Approximately 30 mL of denatured ethanol was used to rinse the silane addition beaker, and this was then added to the hydrolyzing aqueous silane solution. The solution was allowed to stir for about one hour at room temperature to thoroughly hydrolyze the silane. 30 parts by weight of a filler blend of 98 parts of quartz filler and 2 parts of fumed silica (Cab-O-Sil M5: Cabot Corp., Tuscola, Ill.) was slowly added to the silane solution. The pH of the resulting dispersion was 4.94 at 36 minutes after filler addition. The slurry was stirred overnight at room temperature before drying for 40 hours in a convection oven at 50° C. The dried cake was pulverized with a mortar and pestle and then shaken through a 74 micron nylon screen in a sealed container on a mechanical shaker. The screened powder was then stored in a one pint glass jar with a foil lined paper seal to reduce moisture vapor transmission.

EXAMPLE 62

A solution of 10 parts water and 10 parts ethanol was adjusted to a pH of 4.5±0.1 by addition of dilute trifluoroacetic acid (pH approximately 0.5). 0.25 parts of 3-glycidoxypropyltrimethoxysilane (G6720: United Chemical Technologies, Bristol, PA) was added under vigorous stirring; the weighing beaker for the silane was rinsed with 20–30 ml of ethanol; then, the preparation was allowed to hydrolyze for 60 min. Next, 20 parts of the filler sample prepared according to Example 21 was added to the silane preparation under vigorous stirring; the slurry pH was 5.23. After allowing the slurry to stir overnight, it was poured into a glass tray and dried at 45–50° C. for 24 h; the resulting cake was hand-crushed and passed through a 74 micrometer nylon screen.

EXAMPLE 63

The filler was prepared by silane treating a portion of the filler sample prepared according to Example 27, 30 ml of a solution of 10 parts water and 10 parts ethanol was adjusted to a pH of 4.5±0.1 by addition of dilute trifluoroacetic acid (pH approximately 0.5). 0.72 parts of 3-glycidoxypropyltrimethoxysilane (G6720: United Chemical Technologies, Bristol, Pa.) was added under vigorous stirring; the weighing beaker for the silane was rinsed with 20–30 ml of ethanol; then, the preparation was allowed to hydrolyze for 60 min. Next, 30 parts of the filler was added to the silane preparation under vigorous. After allowing the slurry to stir overnight, it was poured into a glass tray and dried at 50° C. for 40 h; the resulting cake was hand-crushed and passed through a 74 micrometer nylon screen.

EXAMPLE 64

The filler was prepared by silane treating a portion of the filler sample prepared according to Example 15. The silanation procedure was the same as for the filler sample of Example 63, except that 0.29 parts of 3-glycidoxypropyltrimethoxysilane were used instead of 0.72 parts.

EXAMPLE 65

The filler prepared as described in Example 41 was ball milled with ¼ inch alumina media and then annealed at 1000° C. for 6 hours. The resulting filler was then silane treated as follows. Deionized water was boiled until the pH reached 5.0–5.6, and then cooled to room temperature. 187 g of this water was mixed with 10 g of ethanol and 2.96 g of glycidoxypropyl trimethoxy silane and the resulting mixture was stirred for 30 minutes. 100 g of the filler was then added to this mixture to form a slurry which was stirred for 2 hours and then dried in an oven for 16 hours at 45° C.

Each filler was used to prepare a composite following the procedure described in Example 1. The resin used in Example 65 was Resin B4. The resin used in Examples A and 62–64 had the following composition:

20.54%(w/w) Heloxy 48 epoxy resin (Shell Chemical Co.);

61.61% (w/w) UVR 6105 epoxy resin;

16% (w/w) pTHF;

1.25% (w/w) CD1012;

0.5% (w/w) CPQ;

0.1 %(w/w) EDMAB.

The hardness (measured using the GYZJ-934-1 meter), compressive strength, diametrile tensile strength, and visual opacity for each composite were evaluated according to Test Procedures A, P, O, and Q, respectively, with the exception that the Barcol values were recorded 5 minutes after removal of the radiation source. The results are shown in Table 15. The designation "—" means not tested.

TABLE 15

| Example | Filler Loading (w/w %) | Barcol | Comp. Strength (MPa) | Diam. Tensile (MPa) | Visual opacity |
|---|---|---|---|---|---|
| A | 80 | 54 | 272 | 75 | 0.53 |
| 62 | 76.7 | 50 | 219 | 56 | — |
| 63 | 78.2 | 43 | 220 | 53 | 0.58 |

TABLE 15-continued

| Example | Filler Loading (w/w %) | Barcol | Comp. Strength (MPa) | Diam. Tensile (MPa) | Visual opacity |
|---|---|---|---|---|---|
| 64 | 78.9 | 50 | 160 | 37 | 0.68 |
| 65 | 70 | 60 | 260 | 71.85 | — |

EXAMPLE 66

This example describes the preparation of radiopaque composites in which the polymer matrix was derived from a vinyl ether. The composites were prepared following the procedure described in Example 1. The resin used in each case was Resin B6. The filler loading in each case was 50% (w/w).

The hardness of each composite was evaluated according to Test Procedure A using the GYZJ-935 meter, with the exception that the Barcol values were recorded immediately following removal of the radiation source. The results are reported in Table 16.

TABLE 16

| Filler | Barcol |
|---|---|
| None | 0 |
| Ex. 20 | 10 |
| Ex. 22' | 30 |

"Ex. 22" means that the filler used in this composite was prepared as described in Example 22 except that it was fired at 900° C. for 4 hours.

The results demonstrate that useful composite can be prepared using vinyl ether resins as the matrix material. Both filled composites exhibited higher Barcol values than the unfilled sample, demonstrating that the filler did not inhibit the cationic polymerization mechanism to any appreciable extent.

EXAMPLES 67–79

These examples describe the preparation of a number of novel filler compositions. The fillers were prepared as follows. Glass frits for each filler were prepared by weighing out appropriate precursors to yield the oxide compositions shown in Table 17. After blending, the batches were heated to 1400–1650° C. for a sufficient time to assure a homogeneous melt, quenched in water, and dried. In all cases, a transparent glass was obtained.

TABLE 17

| Example | Al2O3 | B2O3 | La2O3 | SiO2 | ZnO | Other |
|---|---|---|---|---|---|---|
| 67 | 5 | 30 | — | 30 | 35 | |
| 68 | 10 | 25 | — | 25 | 40 | |
| 69 | 15 | 25 | 10 | 35 | 15 | |
| 70 | 15 | 20 | 5 | 40 | 20 | |
| 71 | 15 | 25 | — | 30 | 30 | |
| 72 | 20 | 20 | 25 | 30 | — | 5Gd2O3 |
| 73 | 20 | 25 | 20 | 35 | — | |
| 74 | 10 | 25 | 30 | 35 | — | |
| 75 | 15 | 30 | 20 | 35 | — | |
| 76 | 15 | 15 | 30 | 20 | — | 20Ta2O5 |
| 77 | 15 | 35 | — | 30 | — | 20Ta2O5 |

TABLE 17-continued

| Example | Al2O3 | B2O3 | La2O3 | SiO2 | ZnO | Other |
|---|---|---|---|---|---|---|
| 78 | 20 | 20 | — | 30 | — | 30Yb2O3 |
| 79 | 10 | 20 | 5 | 40 | 25 | |

All values reported in Table 17 are given in weight %.

The properties of the fillers shown in Table 17 were evaluated according to Test Procedures J, L, and M. The results are reported in Table 18. The designation "—" means not tested.

TABLE 18

| Example | XRD | Fluorescence | $n_D$ |
|---|---|---|---|
| 67 | Am + very weak unid. ph. | N | 1.585 |
| 68 | — | — | 1.599 |
| 69 | — | N | 1.570 |
| 70 | — | N | 1.560 |
| 71 | — | — | — |
| 72 | — | B/w | — |
| 73 | — | B/w | 1.558 |
| 74 | — | B/w | 1.596 |
| 75 | — | N | 1.541 |
| 76 | — | N | 1.680 |
| 77 | — | N | — |
| 78 | — | N | — |
| 79 | — | N | 1.600 |

Other embodiments are within the following claims.

What is claimed is:

1. A method of preparing a polymerized composition comprising:
    (a) providing a polymerizable composition comprising:
        (i) a cationically active functional group;
        (ii) an initiation system capable of initiating cationic polymerization of said cationically active functional group; and
        (iii) a filler composition comprising a radiopacifying filler selected from the group consisting of metal oxides, metal halides, metal borates, metal phosphates, metal silicates, metal carbonates, metal germanates, metal tetrafluoroborates, metal hexafluorophosphates, and combinations thereof, in an amount sufficient to render said polymerizable composition radiopaque,
    components (i), (ii), and (iii) being selected such that said polymerizable composition is capable of polymerizing to form a polymerized composition having a Barcol hardness, measured using a GYZJ-935 meter, of at least 10 within 30 minutes following initiation of said cationically active functional group at a reaction temperature of 25° C.;
    wherein said filled composition is selected such that when the amount of said radiopacifying filler is at least 50% by weight of said polymerizable composition, said radiopacifying filler has an isoelectric point, measured according to the Isoelectric Point Test Procedure, of no greater than 7; and
    (b) initiating polymerization of said cationically active functional group to form said polymerized composition.

2. A method according to claim 1 comprising initiating polymerization of said cationically active functional group at a reaction temperature of 37° C. or less.

3. A method according to claim 1 wherein said initiation system comprises a photoinitiation system, said method comprising exposing said polymerizable composition to actinic radiation to initiate polymerization of said cationically active functional group.

4. A method according to claim 3 wherein said photoinitiation system comprises a visible light sensitizer, said method comprising exposing said polymerizable composition to visible radiation to initiate polymerization of said cationically active functional group.

5. A method according to claim 1 wherein said initiation system comprises a thermal initiation system, said method comprising exposing said polymerizable composition to thermal radiation to initiate polymerization of said cationically active functional group.

6. A method according to claim 1 wherein said polymerized composition comprises a dental composite.

7. A method of preparing a photopolymerized dental composite comprising:

(a) providing a photopolymerizable dental composite comprising:
(i) a cationically active functional group;
(ii) a photoinitiation system capable of initiating cationic polymerization of said cationically active functional group; and
(iii) a filler composition comprising a radiopacifying filler in an amount sufficient to render said dental composite radiopaque, components (i), (ii), and (iii) being selected such that upon exposure to visible light said photopolymerizable composite polymerizes to form a polymerized dental composite having a Barcol hardness, measured using a GYZJ-935 meter, of at least 10 within 30 minutes following initiation of said cationically active functional group at a reaction temperature of 25° C., wherein said filler composition is selected such that when the amount of said radiopacifying filler is at least 50% by weight of said photopolymerizable composite, said radiopacifying filler has an isoelectric point, measured according to the Isoelectric Point Test Procedure, of no greater than 7; and (b) initiating polymerization of said cationically active functional group to form said polymerized dental composite.

8. A method of preparing a polymerized composition comprising:

(a) providing a polymerizable composition comprising:
(i) a cationically active functional group;
(ii) an initiation system capable of initiating cationic polymerization of said cationically active functional group; and
(iii) a filler composition comprising a radiopacifying filler selected from the group consisting of metal oxides, metal halides, metal borates, metal phosphates, metal silicates, metal carbonates, metal germanates, metal trifluoroborates, metal hexafluorophosphates, and combinations thereof, in an amount sufficient to render said polymerizable composition radiopaque, components (i), (ii), and (iii) being selected such that said polymerizable composition is capable of polymerizing to form a polymerized composition having a Barcol hardness, measured using a GYZJ-935 meter, of at least 10 within 30 minutes following initiation of said cationically active functional group at a reaction temperature of 25° C., wherein said filler composition is selected such that (A) when the amount of said filler composition is 50% by weight of said polymerizable composition, a test polymerizable composition according to the Adsorption Isotherm Analysis Test Procedure that includes said filler composition has an adsorption value of no greater than about 80 micromoles/g filler, as determined by the surface area titration according to the Adsorption Isotherm Analysis Test Procedure; and/or (B) when the amount of said filler composition is 70% by weight of said polymerizable composition, a test polymerizable composition according to the Adsorption Isotherm Test Procedure that includes said filler composition has an adsorption value of no greater than about 20 micromoles/g filler, as determined by surface area titration according to the Adsorption Isotherm Analysis Test Procedure; and (b) initiating polymerization of said cationically active functional group to form said polymerized composition.

9. A method of preparing a polymerized composition comprising:

(a) providing a polymerizable composition comprising:
(i) a cationically active functional group;
(ii) an initiation system capable of initiating cationic polymerization of said cationically active functional group; and
(iii) a filler composition comprising a radiopacifying filler selected from the group consisting of metal oxides, metal halides, metal borates, metal phosphates, metal silicates, metal carbonates, metal germanates, metal tetrafluoroborates, metal hexafluorophosphates, and combinations thereof, in an amount sufficient to render said polymerizable composition radiopaque, components (i), (ii), and (iii) being selected such that said polymerizable composition is capable of polymerizing to form a polymerized composition having a Barcol hardness, measured using a GYZJ-935 meter, of at least 10 within 30 minutes following initiation of said cationically active functional group at a reaction temperature of 25° C., wherein said filler composition is selected such that: (A) when the amount of said filler composition is 50% by weight of said polymerizable composition, said filler composition causes a change in conductivity of a test solution of no greater than 125 mV, according to the Conductivity Test Procedure; and/or (B) when the amount of said filler composition is 70% by weight of said polymerizable composition, said filler composition causes a change in conductivity of a test solution of no greater than 60 mV, determined according to the Conductivity Test Procedure; and (b) initiating polymerization of said cationically active functional group to form said polymerized composition.

10. A method of preparing a polymerized composition comprising:

(a) providing a polymerizable composition comprising:
(i) a cationically active functional group;
(ii) an initiation system capable of initiating cationic polymerization of said cationically active functional group; and
(iii) a filler composition comprising a radiopacifying filler selected from the group consisting of metal oxides, metal halides, metal borates, metal phosphates, metal silicates, metal carbonates, metal germanates, metal tetrafluoroborates, metal hexafluorophosphates, and combinations thereof, in an amount sufficient to render said polymerizable composition radiopaque, components (i), (ii), and (iii) being selected such that said polymerizable composition is capable of polymerizing to form a polymerized composition having a Barcol hardness, measured using a GYZJ-935 meter, of at least 10 within 30 minutes following initiation of said cationically active functional group at a reaction temperature of 25° C., wherein said filler composition is selected such that said filler composition has a relative peak height of greater than 80% as determined by Fourier Transform Infrared Spectroscopy (FTIR) according to the FTIR Analysis Test Procedure; and (b) initiating polymerization of said cationically active functional group to form said polymerized composition.

* * * * *

UNITED STATES PATENT AND TRADEMARK OFFICE
CERTIFICATE OF CORRECTION

PATENT NO.    : 6,465,541 B2
DATED         : October 15, 2002
INVENTOR(S)   : Bretscher, Kathryn R.

It is certified that error appears in the above-identified patent and that said Letters Patent is hereby corrected as shown below:

Title page,
Item [56], References Cited, OTHER PUBLICATIONS, delete "Mcraw-Hill" and insert in place thereof -- McGraw-Hill --; and delete "*Stonatol. Coll., 4 hu th*" and insert in place thereof -- *Stomatol. Coll., 4$^{th}$* --.
Item [57], ABSTRACT, delete "composition" and insert in place thereof -- compositions --; and last two lines, delete "functional group are" and insert in place thereof -- functional group at --.

Figure 3B:
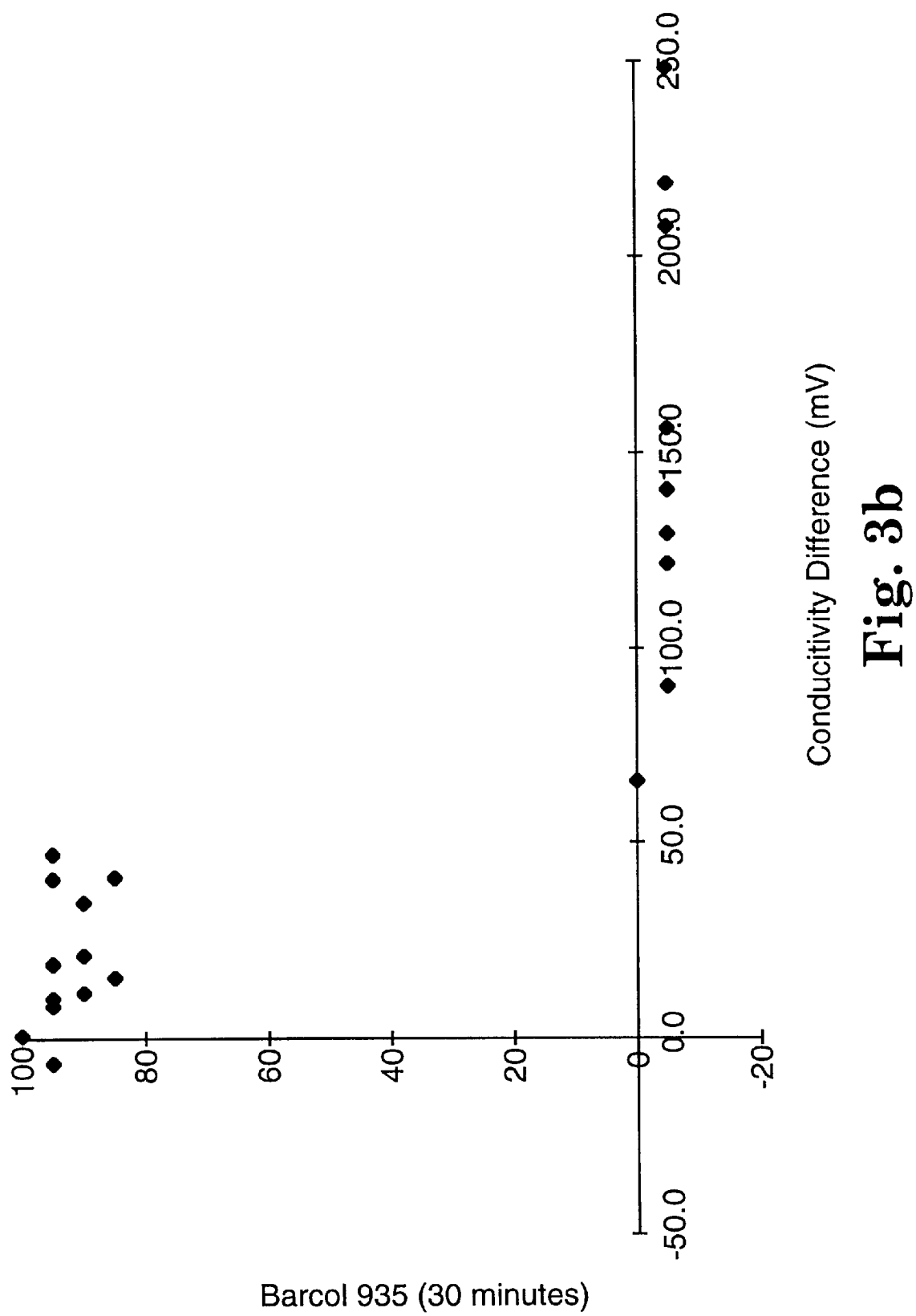

Drawings,
Fig. 3b, delete "Conductivity" and insert in place thereof -- Conductivity --.
Fig. 5, delete "Barcol l(934; 30m)" and insert in place thereof -- Barcol (934, 30 m) --.

Column 2,
Line 20, delete "20" and insert in place thereof -- 20° --.
Line 29, delete "IS04049" and insert in place thereof -- ISO 4049 --.

Column 3,
Line 8, delete "have" and insert in place thereof -- having --.
Line 61, delete "prepared" and insert in place thereof -- prepare --.

Column 4,
Line 13, delete "hafilium" and insert in place thereof -- hafnium --.
Line 33, delete "ar" and insert in place thereof -- are --.

Column 5,
Line 19, delete "is" preceding "melt".

Column 8,
Line 10, after "diffraction." please start a new paragraph.
Line 31, insert -- 30 -- preceding "minutes".

Column 10,
Line 5, "delete "$C(SO_2CF_3)^{3-}$" and insert in place thereof -- $C(SO_2CF_3)_3^-$ --.

Column 11,
Line 51, delete "dimethylaminiophenethanol" and insert in place thereof -- dimethylaminophenethanol --.

UNITED STATES PATENT AND TRADEMARK OFFICE
CERTIFICATE OF CORRECTION

PATENT NO. : 6,465,541 B2
DATED : October 15, 2002
INVENTOR(S) : Bretscher, Kathryn R.

It is certified that error appears in the above-identified patent and that said Letters Patent is hereby corrected as shown below:

Column 12,
Line 19, delete "diphenlyiodonium" and insert in place thereof -- dephenyliodonium --.

Column 13,
Line 61, delete "2,2-b is-" and insert in place thereof -- 2,2-bis- --.

Column 14,
Line 31, insert -- ( -- preceding "e.g.,".

Column 15,
Line 12, delete "oxctanes" and insert in place thereof -- oxetanes --.
Line 28, delete "pentaeiythritol" and insert in place thereof -- pentaerythritol --.
Line 39, delete "," following "these".

Column 18,
Line 64, delete the second occurrence of "the".

Column 19,
Line 34, delete "systems" and insert in place thereof -- system --.

Column 20,
Line 22, delete "(δ)" and insert in place thereof -- Γ --.
Line 43, delete "Coming" and insert in place thereof -- Corning --.
Line 48, delet "XL$_{3000}$$^{TM}$" and insert in place thereof -- XL3000$^{TM}$ --.

Column 21,
Line 17, delete "P$^{H,1726}$]." and insert in place thereof -- P$_{H,1726}$]. --.
Line 38, delete "Fisher" and insert in place thereof -- Fischer --.
Line 44, insert -- in -- preceding "a".
Line 55, delete "Brinauer" and insert in place thereof -- Brunauer --.
Line 60, delete "200" and insert in place thereof -- 200° --.

Column 24,
Line 36, delete "Barol" and insert in place thereof -- Barcol --.

Column 25,
Line 7, insert -- 20 -- preceding "parts".

Column 26,
Line 41, delete "roiling" and insert in place thereof -- rolling --.

UNITED STATES PATENT AND TRADEMARK OFFICE
CERTIFICATE OF CORRECTION

PATENT NO.     : 6,465,541 B2
DATED          : October 15, 2002
INVENTOR(S)    : Bretscher, Kathryn R.

It is certified that error appears in the above-identified patent and that said Letters Patent is hereby corrected as shown below:

Column 28,
Line 37, delete "The designation"—means" and insert in place thereof -- The designation "--" means --.
Line 48, delete "Fisher" and insert in place thereof -- Fischer --.

Column 29,
Line 5, delete "Fisher" and insert in place thereof -- Fischer --.
Line 53, delete "," following "each".

Column 30,
Line 47, delete "(c)" and insert in place thereof -- (e) --.

Column 34,
Line 21, delete "(l)" and insert in place thereof -- (f) --.
Line 51, delete "Coming" and insert in place thereof -- Corning --.
Line 67, delete "Spcx" and insert in place thereof -- Spex --.

Column 35,
Line 59, delete "3 0" following "In".

Column 36,
Line 2, delete "1 000°" and insert in place thereof -- 1000° --.

Column 37,
Line 45, delete "1 050°" and insert in place thereof -- 1050° --.
Line 66, delete "Pyrex M" and insert in place thereof -- Pyrex[TM] --.

Column 40,
Line 63, please insert -- 20 -- following "Example".

Column 41,
Line 42, please insert -- to -- preceding "Test".

Column 43,
Line 12, please insert -- 1. -- following "Example".

UNITED STATES PATENT AND TRADEMARK OFFICE
CERTIFICATE OF CORRECTION

PATENT NO. : 6,465,541 B2
DATED : October 15, 2002
INVENTOR(S) : Bretscher, Kathryn R.

It is certified that error appears in the above-identified patent and that said Letters Patent is hereby corrected as shown below:

Column 51,
Line 55, delete "trifluoroborates" and insert in place thereof -- tetrafluoroborates --.

Signed and Sealed this

Seventeenth Day of August, 2004

JON W. DUDAS
*Acting Director of the United States Patent and Trademark Office*